(12) United States Patent
Li et al.

(10) Patent No.: US 10,874,326 B2
(45) Date of Patent: Dec. 29, 2020

(54) SYSTEM AND METHOD FOR FAST IMAGING IN MAGNETIC RESONANCE IMAGING

(71) Applicant: SHANGHAI UNITED IMAGING HEALTHCARE CO., LTD., Shanghai (CN)

(72) Inventors: Guobin Li, Shanghai (CN); Chaohong Wang, Shanghai (CN); Zhaopeng Li, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 0 days.

(21) Appl. No.: 16/531,274

(22) Filed: Aug. 5, 2019

(65) Prior Publication Data

US 2019/0350487 A1 Nov. 21, 2019

Related U.S. Application Data

(63) Continuation of application No. 15/321,882, filed as application No. PCT/CN2016/078666 on Apr. 7, 2016, now Pat. No. 10,368,778.

(51) Int. Cl.
*G01V 3/00* (2006.01)
*A61B 5/055* (2006.01)
*G01R 33/00* (2006.01)
*G01R 33/022* (2006.01)
*G01R 33/48* (2006.01)
*G01R 33/561* (2006.01)

(52) U.S. Cl.
CPC ............. *A61B 5/055* (2013.01); *G01R 33/00* (2013.01); *G01R 33/022* (2013.01); *G01R 33/482* (2013.01); *G01R 33/4824* (2013.01); *G01R 33/5617* (2013.01)

(58) Field of Classification Search
CPC ............. G01R 33/543; G01R 33/5659; G01R 33/3415; G01R 33/36; A61B 5/055
USPC ........................................................ 324/309
See application file for complete search history.

(56) References Cited

U.S. PATENT DOCUMENTS 5,561,370 A 10/1996 Fuderer
5,883,514 A 3/1999 Ishikawa
(Continued)

FOREIGN PATENT DOCUMENTS

CN 103961097 A 8/2014
WO 2004099809 A1 11/2004

OTHER PUBLICATIONS

International Search Report in PCT/CN2016/078666 dated Mar. 28, 2017, 5 pages.
(Continued)

*Primary Examiner* — Walter L Lindsay, Jr.
*Assistant Examiner* — Frederick Wenderoth
(74) *Attorney, Agent, or Firm* — Metis IP LLC

(57) ABSTRACT

A system and method for magnetic resonance imaging is provided. The method includes generating a main magnetic field through a region of interest (ROI), applying a slice selection gradient to an slice of the ROI, applying a plurality of RF pulses to the slice to generate a plurality of echoes, applying a first encoding gradient and a second encoding gradient on the echoes, and generating MR images based on the echoes.

20 Claims, 16 Drawing Sheets

(56) References Cited

U.S. PATENT DOCUMENTS

| | | | | |
|---|---|---|---|---|
| 5,926,022 | A * | 7/1999 | Slavin | G01R 33/5615 324/300 |
| 2006/0238193 | A1 | 10/2006 | Roberts et al. | |
| 2006/0273945 | A1 * | 12/2006 | Bauer | H03M 1/1255 341/155 |
| 2008/0284439 | A1 | 11/2008 | Xu et al. | |
| 2009/0273345 | A1 * | 11/2009 | Ruhm | G01R 33/3415 324/309 |
| 2009/0326367 | A1 * | 12/2009 | Doyle | G01R 33/5616 600/413 |
| 2010/0176810 | A1 * | 7/2010 | Bolster, Jr. | G01R 33/56358 324/309 |
| 2011/0006768 | A1 | 1/2011 | Ying et al. | |
| 2011/0031971 | A1 | 2/2011 | Deimling et al. | |
| 2011/0241668 | A1 * | 10/2011 | Beckmann | A61B 5/015 324/307 |
| 2013/0278254 | A1 | 10/2013 | Reeder et al. | |
| 2014/0111201 | A1 | 4/2014 | Kim et al. | |
| 2014/0184221 | A1 | 7/2014 | Son et al. | |
| 2014/0197834 | A1 * | 7/2014 | Porter | G01R 33/4818 324/309 |
| 2015/0108976 | A1 | 4/2015 | Fischer et al. | |
| 2016/0169999 | A1 * | 6/2016 | Herza | A61B 5/055 600/411 |

OTHER PUBLICATIONS

Written Opinion in PCT/CN2016/078666 dated Mar. 28, 2017, 5 pages.

Extended European Search Report in European Application No. 16876982.6 dated Jun. 14, 2018, 10 pages.

J. Henning et al., RARE Imaging: A Fast Imaging Method for Clinical MR, Magnetic Resonance in Medicine, 3: 823-833, 1986.

E. M. Haacke et al., A Fast, Iterative, Partial-Fourier Technique Capable of Local Phase Recovery, Journal of Magnetic Resonance, 92: 126-145, 1991.

Daniel Sodickson et al., Simultaneous Acquisition of Spatial Harmonics (SMASH): Fast Imaging with Radiofrequency Coil Arrays, Magnetic Resonance in Medicine, 38: 591-603, 1997.

Klaas P. Pruessmann et al., SENSE: Sensitivity Encoding for Fast MRI, Magnetic Resonance in Medicine, 42: 952-962, 1999.

Mark A. Griswold et al., Generalized Autocalibrating Partially Parallel Acquisitions (GRAPPA), Magnetic Resonance in Medicine, 47: 1202-1210, 2002.

Michael Lustig et al., Sparse MRI: The Application of Compressed Sensing for Rapid MR Imaging, Magnetic Resonance in Medicine, 53: 1182-1195, 2007.

Craig H. Meyer et al., Fast Spiral Coronary Artery Imaging, Magnetic Resonance in Medicine, 28: 202-213, 1992.

James G. Pipe, Motion Correction With PROPELLER MRI: Application to Head Motion and Free-Breathing Cardiac Imaging, Magnetic Resonance in Medicine, 42: 963-969, 1999.

Hisamoto Moriguchi et al., Bunched Phase Encoding (BPE): A New Fast Data Acquisition Method in MRI, Magnetic Resonance in Medicine, 55: 633-648, 2006.

Jeffrey A. Fessler, On NUFFT-based Gridding for Non-Cartesian MRI, J Magn Reson, 188(2) 191-195, 2007.

Rebecca J. Theimann et al., View-Ordering in Radial Fast Spin-Echo Imaging, Magnetic Resonance in Medicine, 51: 768-774, 2004.

Lawrence R. Frank et al., High Efficiency, Low Distortion 3D Diffusion Tensor Imaging with Variable Density Spiral Fast Spin Echoes, NeuroImage, 49: 1510-1523, 2010.

Dong-Hyun Kim et al., Simple Analytic Variable Density Spiral Design, Magnetic Resonance in Medicine, 50: 214-219, 2003.

Matthias Seeger et al., Optimization of K-Space Trajectories for Compressed Sensing by Bayesian Experimental Design, Magnetic Resonance in Medicine. 63: 116-126, 2010.

* cited by examiner

SYSTEM AND METHOD FOR FAST IMAGING IN MAGNETIC RESONANCE IMAGING

CROSS-REFERENCE TO RELATED APPLICATIONS

This application is a Continuation of U.S. application Ser. No. 15/321,882, filed on Dec. 23, 2016, which is a U.S. national stage under 35 U.S.C. § 371 of International Application PCT/CN2016/078666, filed on Apr. 7, 2016, designating the United States of America, the entire contents of which are incorporated herein by reference.

TECHNICAL FIELD

The present disclosure generally relates to magnetic resonance imaging (MRI), and more particularly, to a system and method for fast imaging in MRI.

BACKGROUND

Magnetic Resonance Imaging (MRI) is a widely used medical technique which produces images of a region of interest (ROI) by exploiting a powerful magnetic field and radio frequency (RF) techniques. When an MRI scan is performed on a subject, various RF pulse sequences may be transmitted through an ROI of the subject. The time of transmitting the RF pulse sequences and receiving MR signals determines the acquisition time (TA) of the MRI scan. Given the high power of those pulse sequences, long time exposure under the RF pulse sequences for a subject may cause physical damages to the subject. Therefore, it is desirable to reduce acquisition time for a concern of safety.

SUMMARY

In a first aspect of the present disclosure, a method for generating a magnetic resonance (MR) image is provided. The method may include generating a main magnetic field through an region of interest (ROI); applying a slice selection gradient to an slice of the ROI; applying a plurality of RF pulses to the slice of the ROI to generate a plurality of echoes; applying a first encoding gradient in a first direction and simultaneously applying a second encoding gradient in a second direction on each echo, wherein the amplitude of the first encoding gradient when acquiring the center region of a k-space being lower than that of the first encoding gradient when acquiring the peripheral region of the k-space; generating a plurality of undersampled k-space data sets based on the encoding gradients; and generating an MR image by applying at least one image reconstruction method to the undersampled k-space data sets.

In a second aspect of the present disclosure, provided herein is a magnetic resonance imaging (MRI) system, the MRI system may comprise an MRI scanner, a control unit, and a processing unit. The MRI scanner may comprise a main magnet field generator configured to generate a main magnetic field through a region of interest (ROI), a gradient field generator configured to apply a slice selection gradient to a slice of the ROI, to generate a first encoding gradient in a first direction, and to generate a second encoding gradient in a second direction, and an RF transmit/receive unit configured to transmit a plurality of RF pulses to the slice of the ROI to generate a plurality of echoes. The gradient magnet field generator may be configured to apply the first encoding gradient in the first direction and the second encoding gradient in the second direction simultaneously on each echo, the amplitude of the first encoding gradient when acquiring the center region of the k-space may be lower than that of the first encoding gradient when acquiring the peripheral region of the k-space.

In some embodiments, the RF pulses may comprise fast spin echo (FSE).

In some embodiments, the waveform of the first encoding gradient in the first direction may include three steady phases and two phases of transition.

In some embodiments, the waveform of the first encoding gradient in the first direction may comprise part of a function having a smooth variation. In some embodiments, the function having a smooth variation may comprise a Gaussian function or a harmonic function.

In some embodiments, the second encoding gradient in the second direction may comprise an oscillating waveform. In some embodiments, the waveform may oscillate in a periodic way an aperiodic way.

In some embodiments, the applying a first encoding gradient in the first direction may comprise: applying at least two different encoding gradients for two different echoes, respectively.

In some embodiments, the first encoding gradient in the first direction may include at least one of a dephasing gradient and rephasing gradient.

In some embodiments, the second encoding gradient in the second direction may include at least one of a dephasing gradient and a rephasing gradient.

In some embodiments, the distribution density of an undersampled k-space data set in the center region of the k-space may be larger than the distribution density of an undersampled k-space data set in the peripheral region of the k-space.

In some embodiments, the image reconstruction method may comprise at least one of compressed sensing, parallel imaging, or partial Fourier reconstruction.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The methods, systems, and/or programming described herein are further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
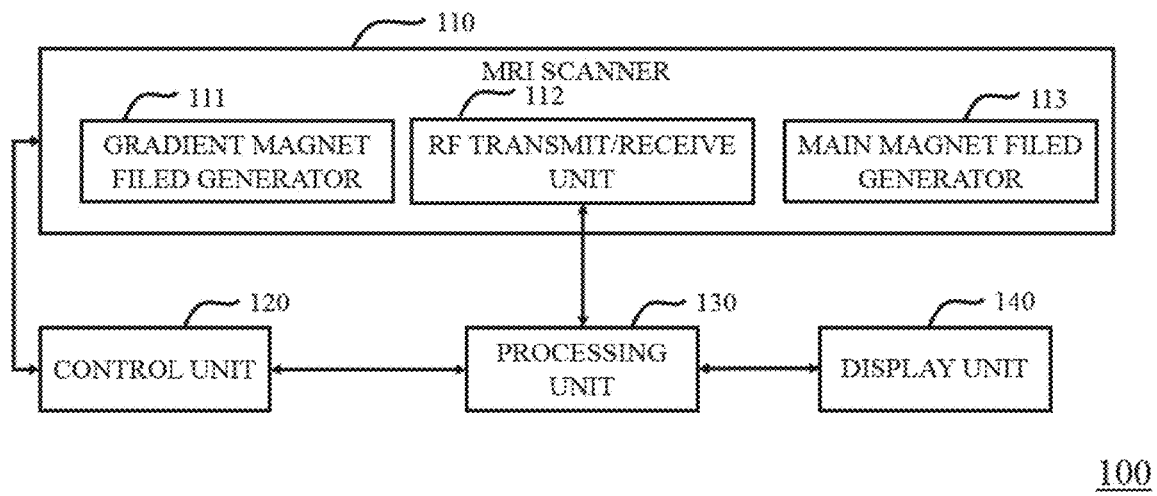
FIG. 1 is a block diagram of a magnetic resonance imaging (MRI) system according to some embodiments of the present disclosure.

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the claims.

It will be understood that when a module or unit is referred to as being "on", "connected to" or "coupled to" another module or unit, it may be directly on, connected or coupled to the other module or unit or intervening module or unit may be present. In contrast, when a module or unit is referred to as being "directly on," "directly connected to" or "directly coupled to" another module or unit, there may be no intervening module or unit present. As used herein, the term "and/or" includes any and all combinations of one or more of the associated listed items.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise" and/or "comprising," when used in this specification, specify the presence of stated features, integers, steps, operations, elements, and/or components, but do not preclude the presence or addition of one or more other features, integers, steps, operations, elements, components, and/or groups thereof.

The present disclosure generally relates to magnetic resonance imaging (MRI), and more particularly, to a system and method for fast imaging in MRI. An MRI image may be generated by manipulating a virtual space called the k-space. The term "k-space," as used herein, may refer to an array of numbers (a matrix) representing spatial frequencies in an MR image. In some embodiments, k-space may be the 2D or 3D Fourier transform of an MR image. The way of manipulating the k-space, referred as k-space sampling, may affect acquisition time (TA). As used herein, the term "acquisition time" may refer to the time to acquire signals of the whole pulse sequence. For example, the term "acquisition time" may refer to the time to obtain the whole k-space data sets from starting filling the k-space. Traditionally, two k-space sampling methods, Cartesian sampling and non-Cartesian sampling, are provided to manipulate k-space. In Cartesian sampling, k-space trajectories are straight lines, while in non-Cartesian sampling, such as radial sampling or spiral sampling, k-space trajectories may be longer than those of Cartesian sampling.

Cartesian sampling may depend on its encoding gradient. Reducing acquisition time in Cartesian sampling may be realized by reducing phase encoding steps and/or increasing analog to digital converter (ADC) bandwidth. However, in Cartesian scanning, the bandwidth of the ADC may be subject to the restriction of the desired spatial resolution and the size of a desired field of view (FOV). In non-Cartesian sampling, as spatial sampling may be performed in multiple dimensions simultaneously, a k-space trajectory may be relatively longer than that of Cartesian sampling.

When non-Cartesian sampling such as radial sampling and spiral sampling, are applied in 2D FSE, artifacts may be generated. On the one hand, in conventional non-Cartesian sampling such as radial sampling and spiral sampling, echoes with different intensity may be filled into k-space and the resulting image may contain streaking artifacts due to, for example, T2-relaxation. On the other hand, in conventional non-Cartesian sampling such as radial sampling and spiral sampling, trajectories may pass through the center region of the k-space. So these trajectories may have equal contribution to the reconstructed image, which may make adjustment of the image contrast difficult.

To reduce data acquisition time, MRI data are often intentionally undersampled. This may, however, lead to reduced SNR (Signal to Noise Ratio) and image degradation.

Non-Cartesian sampling may have advantages over Cartesian sampling as it may have longer k-space trajectories, and more data may be sampled when one echo is acquired. To timely receive the sampled data, the bandwidth of ADC may need to be increased. However, the bandwidth may be subject to limitations of some physical properties including, for example, SNR.

Consequently, it is desirable to develop a system and method capable of reducing acquisition time in 2D FSE using non-Cartesian sampling alone or in combination with some image reconstruction methods.

FIG. 1 is a block diagram of a magnetic resonance imaging system according to some embodiments of the present disclosure. As illustrated, an MRI system 100 may include an MRI scanner 110, a control unit 120, a processing unit 130, and a display unit 140. The MRI scanner 110 may include a gradient magnet field generator 111, a radio frequency (RF) transmit/receive unit 112, and a main magnet field generator 113. The main magnet field generator 113 may create a static magnetic field B0 during an MRI process. The main magnet may be of various types including, for example, a permanent magnet, a superconducting electromagnet, a resistive electromagnet, etc. The gradient magnet field generator 111 may generate magnet field gradients to the main magnet field B0 in the x, y, and/or z directions. The gradient magnet field may encode the spatial information of a subject located in the MRI scanner 110.

The RF transmit/receive unit 112 may include RF transmitting coils and/or receiving coils. These RF coils may transmit RF signals to or receive MR signals from a region of interest (ROI). In some embodiments, the receiving coil and the transmitting coil may be the same one, or they may be different. In some embodiments, the function, size, type, geometry, position, amount, and/or magnitude of the gradient magnet field generator 111 and/or the main magnet field generator 113 and/or of the RF transmit/receive unit 112 may be determined or changed according to one or more specific conditions. For example, according to the difference in function and size, the RF coils may be classified as volume coils and local coils. In some embodiments of the present disclosure, the volume coils may include birdcage coils, transverse electromagnetic coils, surface coils, saddle coils, etc. In some embodiments of the present disclosure, the local coils may include birdcage coils, solenoid coils, saddle coils, flexible coils, etc. In some embodiments, a multi-channel array coil having a plurality of coil elements (sometimes called phased array coils) may be employed in the present disclosure to receive MR signals. Specifically, the multi-channel array coil may be used to perform parallel imaging by simultaneously receiving MR signals in each channel.

The control unit 120 may control the gradient magnet field generator 111 and/or the main magnet field generator 113 and/or the RF transmit/receive unit 112 of the MRI scanner 110, the processing unit 130, and/or the display unit 140. The control unit 120 may receive information from or send information to the MRI scanner 110, the processing 130, and/or the display unit 140. According to some embodiments of the present disclosure, the control unit 120 may receive commands from the display unit 140 provided by, e.g., a user, and adjust the gradient magnet field generator 111 and/or the main magnet field generator 113 and/or RF transmit/receive unit 112 to take images of an ROI according to the received commands.

In some embodiments, depending on the type of magnet used in the main magnet generated by the main magnet field generator 113, the control unit 120 may provide certain control signals to the gradient magnet field generator 111 and/or the main magnet field generator 113 to control various parameters of the main magnetic field that is generated by the main magnet field generator 113. In some embodiments, the control unit 120 may provide instructions for the gradient magnet field generator 111 and/or the main magnet field generator 113 to generate a particular gradient waveform sequence. In some embodiments, the control unit 120 may provide instructions for the RF transmit/receive unit 112 to generate a particular pulse sequence and/or receive the MR signal from the ROI. In some embodiments, the control unit 120 may provide timing information to the processing unit 130, including the length of data acquisition, the type of k-space data acquisition that is used, or the like, for sampling data from the RF transmit/receive unit 112. In some embodiments, the control unit 120 may provide reconstruction information to the processing unit 130 to transform k-space data into images.

The processing unit 130 may process different kinds of information received from different units. For further understanding the present disclosure, several examples are given below, but the examples do not limit the scope of the present disclosure. According to some embodiments of the present disclosure, for example, the processing unit 130 may acquire data from the RF transmit/receive unit to fill the k-space according to the commands or instructions from the control unit 120. The processing unit 130 may also receive information to transform k-space data into frequency-domain data, which may be a two-dimensional (2-D) or three-dimensional (3-D) data set. As used herein, the term "frequency-domain data" may refer to the data displayed in the frequency domain in which the feature of how much of a signal lies within each given frequency band over a range of frequencies may be displayed. The processing unit 130 may also receive the information to map or transform the frequency-domain data into optical data. For example, in a monochrome display, the frequency-domain data may be mapped or transformed into the luminance values of pixels. In a color display, frequency-domain data may be mapped or transformed into the luminance and false-color values of pixels. The process unit 130 may also receive the information to transform the optical data into signals, which may be displayed as the image viewed by a user. In some embodiments, the processing unit 130 may process data provided by a user or an operator via the display unit 140 and transform the data into specific commands or instructions (for example, computer-readable commands or instructions), and supply the commands or instructions to the control unit 120.

The display unit 140 may receive input and/or display output information. The input and/or output information may include programs, software, algorithms, data, text, number, images, voice, or the like, or any combination thereof. For example, a user or an operator may input some initial parameters or conditions to initiate a scan. As another example, some information may be imported from external resource, such as a floppy disk, a hard disk, a wireless terminal, or the like, or any combination thereof.

It should be noted that the above description of the MRI system 100 is merely provided for the purposes of illustration, and not intended to limit the scope of the present disclosure. For persons having ordinary skills in the art, multiple variations and modifications may be made under the teachings of the present disclosure. For example, the assembly and/or function of the MRI system 100 may be varied or changed according to specific implementation scenarios. Merely by way of example, some other components may be added into the MRI system 100, such as a subject positioning unit, a gradient amplifier unit, and other devices or units. Note that the MRI system may be a traditional or a single-modality medical system, or a multi-modality system including, e.g., a positron emission tomography-magnetic resonance imaging (PET-MRI) system, a computed tomography-magnetic resonance imaging (CT-MRI) system, a remote medical MRI system, and others, etc. However, those variations and modifications do not depart from the scope of the present disclosure.

Figure 2:
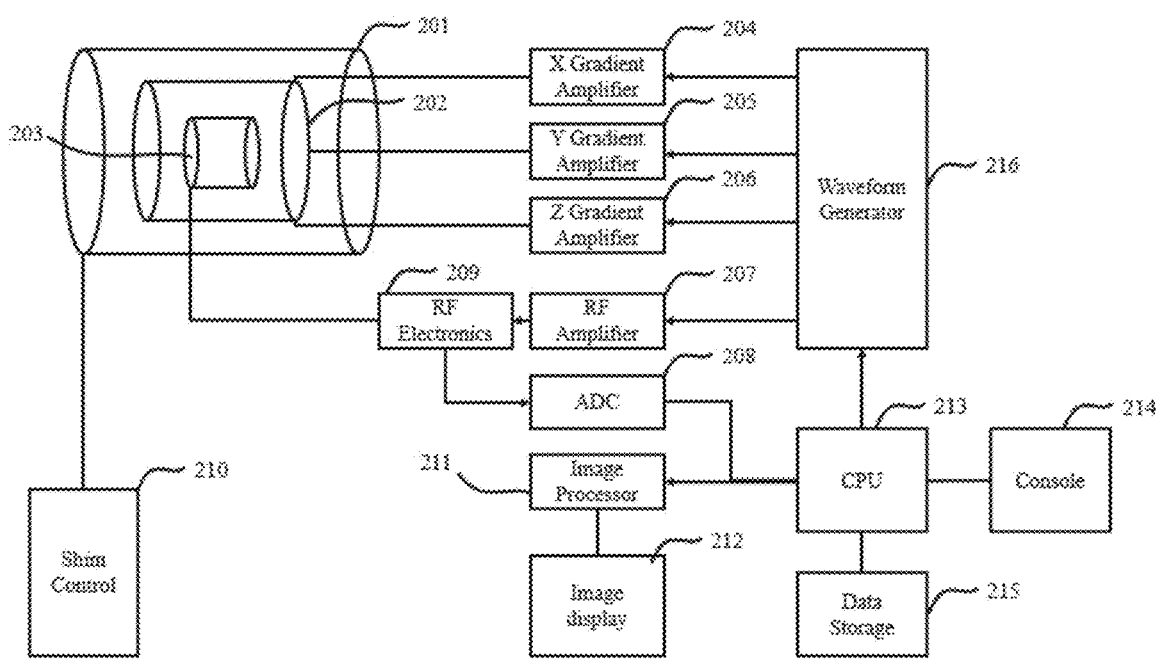
FIG. 2 is a block diagram of an MRI system according to some embodiments of the present disclosure.

FIG. 2 is a block diagram of the MRI system 100 according to some embodiments of the present disclosure. As shown in the figure, the main field and shim coils 201 may generate a main magnetic field that may be applied to an object exposed inside the field. The main field and shim coils 201 may also control the homogeneity of the generated main field. Gradient coils 202 may be located inside the main field and shim coils 201. The gradient coils 202 may generate a second magnetic field or referred to as a gradient field. The gradient coils 202 may distort the main field generated by the main field and shim coils 201 so that the magnetic orientations of the protons of an object may vary as a function of their positions inside the gradient field. The gradient coils 202 may include X coils, Y coils, and/or Z coils (not shown in the figure). In some embodiments, the Z coils may be designed based on circular (Maxwell) coils, while the X coils and the Y coils may be designed on the basis of the saddle (Golay) coil configuration. The three sets of coils may generate three different magnetic fields that are used for position encoding. The gradient coils 202 may allow spatial encoding of MR signals for image construction. The gradient coils 202 may be connected with one or more of an X gradient amplifier 204, a Y gradient amplifier 205, or a Z gradient amplifier 206. One or more of the three amplifiers may be connected to a waveform generator 216. The waveform generator 216 may generate gradient waveforms that are applied to the X gradient amplifier 204, the Y gradient amplifier 204, and/or the Z gradient amplifier 204. An amplifier may amplify a waveform. An amplified waveform may be applied to one of the coils in the gradient coils 202 to generate a magnetic field in the x-axis, the y-axis, or the z-axis, respectively. The gradient coils 202 may be designed for either a close-bore MRI scanner or an open-bore MRI scanner. In some instances, all three sets of coils of the gradient coils 202 may be energized and three gradient fields may be generated thereby. In some embodiments of the present disclosure, the X coils and Y coils may be energized to generate the gradient fields in the x-direction and the y-direction.

RF (radio frequency) coils 203 may generate a third magnetic field that is utilized to generate MR signals for image construction. In some instances, the RF coils 203 may include a transmitting coil and a receiving coil. In some embodiments, the RF coils 203 may be in connection with RF electronics 209 that may be configured or used as one or more integrated circuits (ICs) functioning as a waveform transmitter and/or a waveform receiver. The RF electronics 209 may be connected with an RF amplifier 207 and an analog-to-digital converter (ADC) 208. The waveform generator 216 may generate an RF signal. The RF signal may be first amplified by the RF amplifier 207, processed by the RF electronics 209, and applied on the RF coils 203 to generate a third magnetic field, in addition to the magnetic fields generated by, e.g., the main field and shim coils 201 and the gradient coils 202. In some embodiments of the present disclosure, the waveform generator 201 may generate a series of RF waveforms periodically or aperiodically. For instance, the waveform generator 216 may generate an excitation RF pulse with a flip angle of 90° and multiple refocusing RF pulses with a flip angle of 180°. Note that the excitation RF pulse may have a flip angle other than 90°, e.g., any magnitude ranging from 0° to 180°. An excitation RF pulse with a flip angle of 90° is mentioned elsewhere in the present disclosure for illustration purposes, and is not intended to limit the scope of the present disclosure.

As described elsewhere in the present disclosure, the flip angle of a refocusing RF pulse may be of a value other than 180°. Furthermore, the waveform generator 216 may generate a series of RF waveforms periodically or aperiodically. For instance, the waveform generator 216 may generate an excitation RF pulse with a flip angle of 90° and multiple refocusing RF pulses with same flip angles or variable flip angles. The flip angle of the excitation RF pulse may be variable as well. The excitation RF pulse may be utilized to generate the third magnetic field, and with the application of one or more refocusing RF pulses, one or more MR signals may be generated. For instance, an echo train with multiple echoes may be generated. The echo train length (ETL) may be either fixed or variable. For instance, for a same tissue to be imaged, ETL may be fixed. For different tissues, ETL may be variable. Furthermore, even for a same tissue, ETL may be variable. The echo train may be received by the receiving coils of the RF coils 203. Then the echo train may be sent to the RF electronics 209, and transmitted to the ADC 208 for digitization. The echo train may be demodulated and filtered in the electronics 209. Subsequently, the echo train may be processed by an image processor 211, e.g., with the assistance of the CPU 213, to generate one or more images. A console 214 may communicate through a link with the CPU 213 and allow one or more operators to control the production and/or display of images on image display 212. The console 214 may include an input device, a control panel (not shown in the figure), etc. The input device may be a keyboard, a touch screen, a mouse, a remote controller, or the like, or any combination thereof.

The CPU 213 may control the production of the waveforms in the waveform generator 216, and the production of images in the image processor 211. The CPU 213 may be a central processing unit (CPU), an application-specific integrated circuit (ASIC), an application-specific instruction-set processor (ASIP), a graphics processing unit (GPU), a physics processing unit (PPU), a microcontroller unit, a digital signal processor (DSP), a field programmable gate array (FPGA), an ARM, or the like, or any combination thereof.

The data storage 215 may store received MR signals. When an MRI scan is completed and the whole data of a scanned object (e.g., a tissue or a specific part of a body) is acquired. A Fourier transform of the data may be performed by, without limitation to, the CPU 213, the image processor 211, or the like, or any combination thereof. After the transform is completed, one or more desired images may be generated. The images may be stored in the data storage 215. The images may be further conveyed to the image display 212 for display. A shim control 210 may be utilized to control the homogeneity of the main magnetic field generated by the main field and shim coils 201.

In some embodiments of the present disclosure, an improved or optimized flip angle schedule may be acquired according to one or more criteria described elsewhere in the present disclosure. A flip angle schedule may include a group of flip angles of refocusing RF pulses. The calculation of flip angles may be performed by the CPU 213. The refocusing RF pulses may be divided into a certain number of phases. Each phase may include one or more refocusing RF pulses. The flip angle(s) of refocusing RF pulse(s) of each phase may be calculated in accordance with one or more equations or functions. A signal evolution may be produced on the basis of the calculated flip angles of the refocusing RF pulses.

It should be noted that the above description of the MRI system is merely provided for the purposes of illustration, and not intended to limit the scope of the present disclosure. For persons having ordinary skills in the art, multiple variations and modifications may be made under the teaching of the present invention. However, those variations and modifications do not depart from the scope of the present disclosure.

Figure 3:
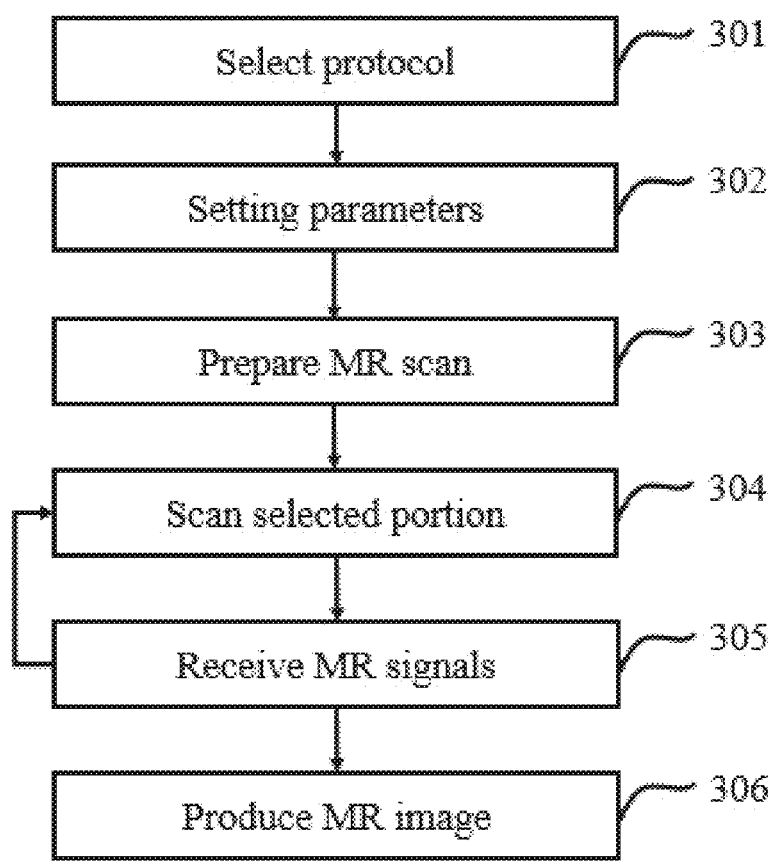
FIG. 3 is a flowchart of an MR scan that may be performed according to some embodiments of the present disclosure.

FIG. 3 depicts a flowchart of an MR scan that may be performed according to some embodiments of the present disclosure. In step 301, one or more protocols may be selected. A protocol may be designed for one or more tissues to be imaged, diseases, and/or clinical scenarios. A protocol may contain a certain number of pulse sequences oriented in different planes and/or with different parameters. The pulse sequences may include spin echo sequences, gradient echo sequences, diffusion sequences, inversion recovery sequences, or the like, or any combination thereof. For instance, the spin echo sequences may include fast spin echo (FSE), turbo spin echo (TSE), rapid acquisition with relaxation enhancement (RARE), half-Fourier acquisition single-shot turbo spin-echo (HASTE), turbo gradient spin echo (TGSE), or the like, or any combination thereof. When an MR scan is to be conducted, an operator may select a protocol for the scan. For example, for a cranial scan, the operator may select any one of the protocols called "Routine Adult Brain," "MR Angiogram Circle of Willis," and many others. These protocols described above or other protocols may be stored in the data storage 215 as discussed in FIG. 2, or other storage devices (e.g., an external storage device or server accessible by the MR system 100).

Parameters may be set in step 302. The parameters may be set via the console 214 through a user interface that may be displayed on, e.g., the image display 212 as specified in FIG. 2. The parameters may include image contrast and/or ratio, an ROI, slice thickness, an imaging type (e.g., T1 weighted imaging, T2 weighted imaging, proton density weighted imaging, etc.), T1, T2, a spin echo type (spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), or the like, or any combination thereof.

According to some embodiments of the present disclosure, the term "phase" may refer to a segment, section, part or fragment of a series of flip angles (or a flip angle schedule) corresponding to an echo train divided according to some principles. The number of phase(s) and/or the number of echo(es) in each phase may depend on specific conditions. In some embodiments, an echo train may be divided into several phases according to considerations including, e.g., the characteristics of a reference signal schedule, a desired signal evolution, etc. Merely by way of example, the reference signal schedule of an echo train may be divided into three segments, regardless of what their values are or how their trends vary (e.g. firstly exponential decay, secondly essentially flat, and lastly exponential decay again), then the echo train may be divided into three phases accordingly. In some embodiments, the reference signal schedule may lack obvious characteristics on the basis of which to divide it into different phases. For example, only one or several specific echo(es) associated with resultant signal(s) of interest need to be paid attention to. For example, it is desired that the signals corresponding to two echoes meet one or more thresholds; the echo train may belong to a single phase so that the two echoes of interest are located in the same phase; the echo train may be divided into two or more phases, and the two echoes of interest may be located in a same phase or different phases. In some embodiments, there may be no reference signal schedule at all, and the number of phase(s) and/or the number of echo(es) in each phase may be determined based on, e.g., a random division, an equal division, a certain rule, or the like, or any combination thereof. The certain rule may include Arithmetic progression, Geometric progression, Cauchy sequence, Farey sequence, look-and-say sequence, or the like, or a variation thereof, or any combination thereof.

It should be noted that the above embodiments are for illustration purposes and not intended to limit the scope of the present disclosure. The determination of the number and length of the phase(s) may be variable, changeable, or adjustable based on the spirits of the present disclosure. For example, the number of phases in an echo train may be one, two, three, or more, or equal to the number of echoes. In some embodiments, several echoes may be located in one phase, and the remaining echoes belong to one or more other phases or are not assigned to a phase at all. However, those variations and modifications do not depart from the scope of the present disclosure.

Preparation for the MR scan may be performed in step 303. The preparation may include placing an object, e.g., a selected portion of an ROI, within the scanning area, setting the scanning range, tuning and matching shimming coils, adjusting a center frequency, adjusting transmitter attenuation/gain, adjusting signal reception attenuation/gain, setting dummy cycles, or the like, or any combination thereof.

The selected portion of an ROI may be scanned in step 304. The scanning may include localizer scans, calibration scans for parallel imaging, automatic pre-scan, or the like, or any combination thereof. For instance, the localizer scans may produce localizer images of low resolution and a large field of view (FOV). Such localizer images may be utilized in subsequent steps. In this step, one or more pulse sequences including, for example, an excitation RF pulse and a series of refocusing RF pulses, may be applied on the selected portion. The flip angles of the refocusing RF pulses may be either fixed or variable. In some embodiments of the present disclosure, the flip angles are not set in step 302 manually. Instead, the flip angles may be calculated automatically and an optimization procedure may be performed for the calculation of the flip angles until a desired signal evolution is achieved.

Generated MR signals may be received in step 305. Step 305 may be performed by the RF coils 203 as described in FIG. 2. The MR signals may correspond to one or more echo trains, or the like. It should be noted that step 305 and step 306 may be repeated until sufficient data to generate an image is acquired or an image is generated. One or more operations may be performed on the MR signals to produce images of the selected portion. The operations may include frequency encoding, phase encoding, reconstruction, or the like, or any combination thereof. The MR signals are sampled depending on the types of the gradient and RF waveforms. Exemplary image reconstruction methods may include parallel imaging, Fourier reconstruction, constrained image reconstruction, compressed sensing, or the like, or a variation thereof, or any combination thereof. As for dimensions, the Fourier transformation may include 1-dimensional (1D) Fourier transformation, 2-dimensional (2D) Fourier transformation, 3-dimensional (3D) Fourier transformation. As for types, the Fourier transformation may include discrete Fourier transformation, inverse Fourier transformation, fast Fourier transformation (FFT), non-uniform fast Fourier transformation (NUFFT), partial Fourier transformation, or the like, or any combination thereof. Exemplary algorithms of partial Fourier transformation may include zero filling, homodyne processing, iterative homodyne processing, or the like, or any combination thereof. Exemplary algorithms of parallel imaging may include simultaneous acquisition of spatial harmonics (SMASH), AUTO-SMASH, VD-AUTO-SMASH, sensitivity encoding (SENSE), generalized auto-calibrating partially parallel acquisitions (GRAPPA), or the like, or any combination thereof. In step 306, one or more images of the selected portion may be produced. The images may be displayed on, e.g., the image display 212 (shown in FIG. 2), or other display devices (e.g., an external display device).

It should be noted that the flowchart described above is provided for the purposes of illustration, not intended to limit the scope of the present disclosure. For persons having ordinary skills in the art, multiple variations and modifications may be reduced to practice in the light of the present disclosure. However, those variations and modifications do not depart from the scope of the present disclosure. For instance, step 301, step 302, and step 303 may be performed sequentially at an order other than that described above in connection with FIG. 3. Alternatively, step 301, step 302, and step 303 may be performed concurrently.

MRI is a non-invasive imaging technique that may use a powerful main magnet field to align the nucleus spins in a subject (or a portion thereof). When the subject is exposed in a magnetic field (main magnet field B0), the nucleus spins of the subject tend to align with field B0, but may still precess at the Larmor frequency. The overall motion of the nucleus spins in the subject, subject to field B0, may be simplified as net magnetization (M) that is the averaged sum of many individual nucleus spins. The net magnetization M may be broken down into a longitudinal component (along the z-axis, aligned with field B0), and a transverse component (within the XY plane). With the effect of main magnet field B0, M may constitute a longitudinal magnetization vector in the macroscopic angle. A second magnetic field, RF field (field B1), may be applied to M, oscillating the Larmor frequency, and causing M to precess away from the field B0 direction. During the excitation by radio frequency, longitudinal magnetization may decrease and transverse magnetization may appear. Merely by way of example, if an excitation RF pulse with a 90° flip angle is applied, when the RF transmitter is turned off, there is no longitudinal magnetization any more, and only transverse magnetization exists. The transverse magnetization may induce a current signal in the RF receiving coils, and the induced current may be referred to as an MR signal.

Figure 4:
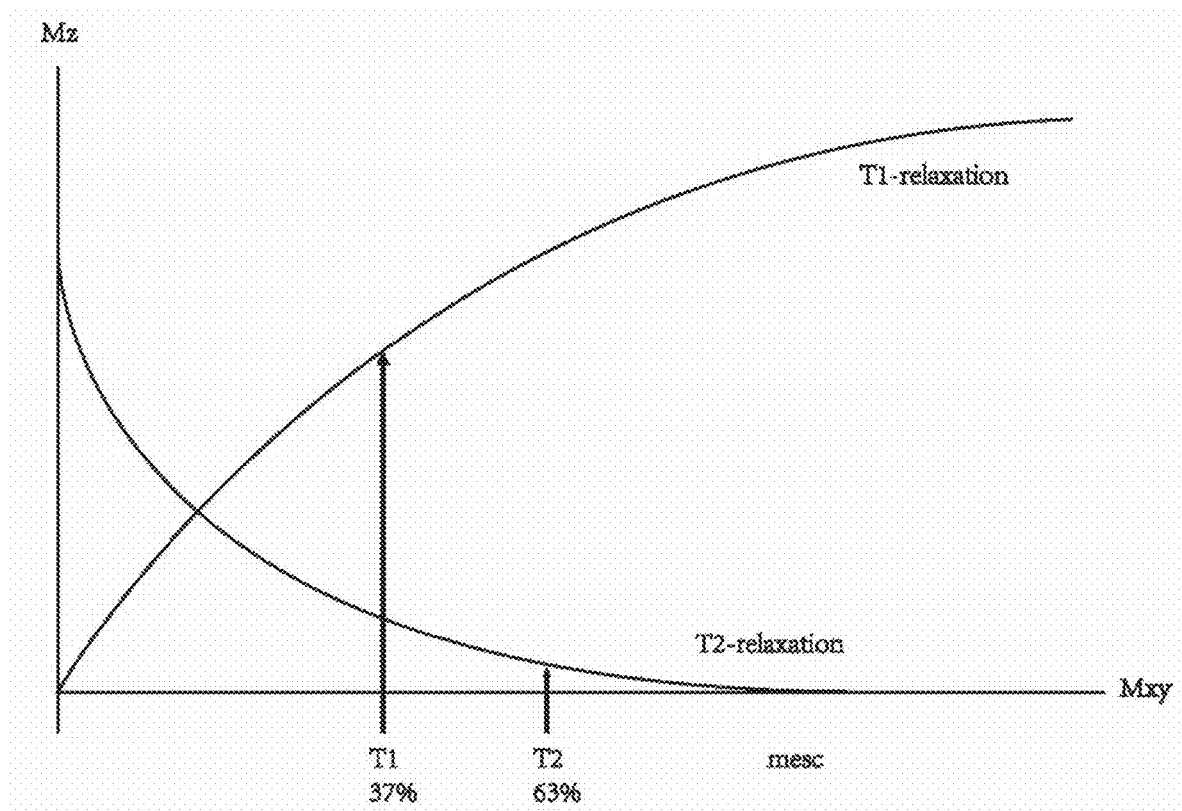
FIG. 4 is a graph illustrating exemplary T1-relaxation and exemplary T2-relaxation in a magnetic resonance imaging process according to some embodiments of the present disclosure.

After the RF excitation with a 90° excitation RF pulse is turned off, the transverse magnetization may decay. Note that the excitation RF pulse may have a flip angle other than 90°, e.g., any magnitude ranging from 0° to 180°. An excitation RF pulse with a flip angle of 90° is mentioned elsewhere in the present disclosure for illustration purposes, and is not intended to limit the scope of the present disclosure. In some embodiments, the decay may be approximated by an exponential curve, which is illustrated by the T2-relaxation shown in FIG. 4. The T2-relaxation (spin-spin relaxation) may be due to spins getting out of phase (or referred to as "dephase"). Since at least some nucleus spins may move together, their magnetic fields may interact with each other, and may cause a change in their precession rate. As these interactions are random and temporary, they may cause an accumulative loss in phase and lead to transverse magnetization decay. T2 may be defined as the time needed for the transverse magnetization to fall to i/e or about 37% of its maximum value in FIG. 4. The T1-relaxation (spin-lattice relaxation) may result from energy exchange between the nucleus spins and their surrounding lattices, during which the spins go from a high energy state toward a thermal equilibrium state. As illustrated in FIG. 4, T1 may be defined as the time needed for the longitudinal magnetization to reach (1−1/e) or about 63% of its maximum value. At the same time, the longitudinal magnetization may recover following approximately an exponential form, which may be referred to as T1-relaxation shown in FIG. 4. It should be noted that for different subjects (e.g., tissues), their T1 and/or T2 are usually different from each other even when they are subject to the same magnet field. For example, with a 1.5 T field strength, T1 of white matter, gray matter, and cerebrospinal fluid (CSF) of the brain are approximately 350~500, 400~600, 3000~4000 milliseconds, respectively. It should also be noted that T1 and T2 may be different from each other for a same tissue of a same subject under a same magnet field. For example, with a 1.5 T field strength, T1 of white matter of the brain may be about 350~500 milliseconds, while T2 of white matter of the brain may be about 90~100 milliseconds, which is shorter than the T1. T2-relaxation may exist regardless of whether there is a T1-relaxation. Some processes may result in or affect T2-relaxation but without affecting T1-relaxation. T1-relaxation may be slower than T2-relaxation. The T1 value may be longer than or equal to the corresponding T2 value.

The T2-relaxation may be exploited to generate an MR signal to image a subject. A spin echo based method may be used in an MRI system to prolong T2 relaxation time. The term "spin echo" or "spin echo sequence" may generally refer to an echo or several echoes formed after the application of, for example, two RF pulses including an excitation RF pulse and a refocusing RF pulse. The spin echo and/or spin echo sequence includes single spin echo, multi-echo spin echo sequence, fast spin echo (FSE, or turbo spin echo (TSE)) sequence, etc.

Merely by way of example of a single spin echo, a 90°-excitation RF pulse may tip the spins into the transverse plane. Then a refocusing RF pulse may turn the spins. The refocusing RF pulse may be used to reduce or prevent the dephasing caused by the non-uniformity of the main magnet field and preserve the real T2-relaxation. The single spin echo may generate one MR signal (e.g., an echo) during the course of the T2-relaxation. The MR signal may be used to generate an image.

As another example, a multi-spin echo sequence may be explained as follows: after the first echo is obtained, there may be an interval until the next repetition time (TR). By applying another refocusing RF pulse, another echo may occur and be detected, with the same phase encoding, to build another image. The other image may be of a different contrast, and may be used in characterizing certain feature of an ROI, e.g., one or more lesions in the ROI. The multi-spin echo may build several images of several slices of the same positioning of a subject without increasing the overall acquisition time by using an interleaved scanning manner. The term "repetition time" or "TR" may refer to the time between the applications of two consecutive excitation RF pulses. The term "slice" here may refer to a planar region being excited by a spatial excitation RF pulse.

Figure 5:
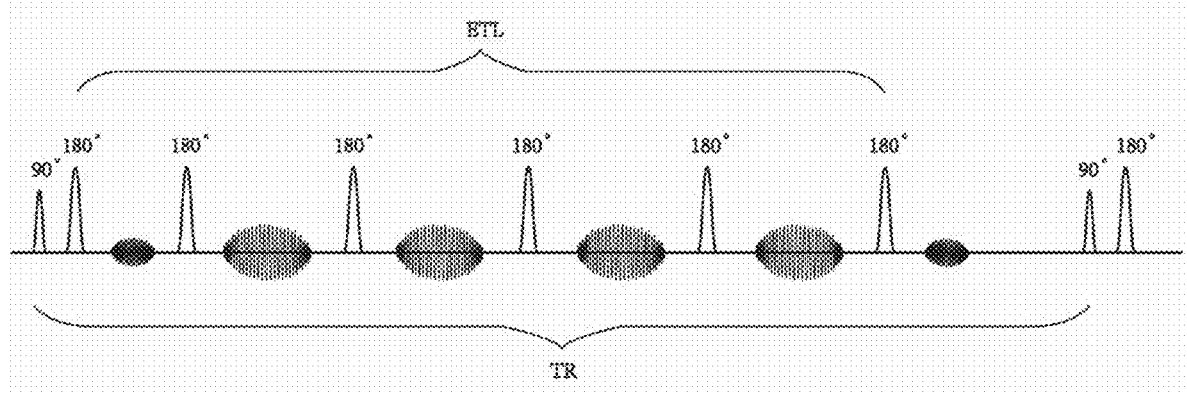
FIG. 5 is a graph illustrating an exemplary echo train for magnetic resonance imaging according to some embodiments of the present disclosure.

FIG. 5 is a graph of an exemplary flip angle schedule applicable in fast spin echo based magnetic resonance imaging according to some embodiments to the present disclosure. According to the fast spin echo technique, after the first echo is detected, within the time interval between the excitation RF pulse and the last refocusing RF pulse within a same TR, an echo train is detected, which may include one or more echoes, to fill the k-space lines in the same slice. Because multiple echoes may be detected within one TR, a number of repetitions needed to fill the k-space may be reduced, the k-space may be filled faster, and the slice acquisition time may be reduced. This may be achieved by applying several 180° refocusing RF pulses to obtain an echo train. As described elsewhere in the present disclosure, the flip angle of a refocusing RF pulse may be of a value other than 180°. After each echo, the phase-encoding may be cancelled and a different phase-encoding may be applied to the following echo. The number of echoes received within a same TR is called the echo train length (ETL). The echo train length (ETL) may be one, two, three, or more than three. In some embodiments, using refocusing RF pulses with flip angles of 180°, the specific absorption rate (SAR) may increase significantly and the T2-relaxation may be remarkable during imaging. In this condition, the ETL may need to be set short, e.g., no more than 30. In some embodiments, using refocusing RF pulses with variable flip angles, the ETL may be longer, e.g., more than 30. The ETL may be several hundred, or higher.

As also illustrated in FIG. 5, in some embodiments of multi-spin echo, echo time (TE) is referred to as the time between the middle of an excitation RF pulse and the middle of the spin echo production. As used herein, "middle" may refer to when the intensity of an echo corresponding to a pulse, e.g., an excitation RF pulse, a refocusing RF pulse, arrives at a maximum value as illustrated in FIG. 5. For a multi-echo train, echo times may be denoted as TE1, TE2, etc. In some embodiments of fast spin echo, as the echoes corresponding to the central k-space lines are the ones that may determine image contrast, the time between the middle of an exciting RF pulse and the middle of the echoes corresponding to the central k-space is called effective echo time (effective TE, or $TE_{eff}$).

In some embodiments according to the present disclosure, the difference in the characteristic, e.g., T1 value, T2 value, and/or proton density (or spin density), among different subjects (e.g., different issues) may provide a basis to show an anatomic structure and/or pathological changes in magnetic resonance imaging. Several weighting imaging types may be used to emphasize above characteristics and build specific images. Exemplary imaging type may include T1 weighted imaging (T1WI), T2 weighted imaging (T2WI), proton density weighted imaging (PDWI), or the like, or any combination thereof. For example, in T1 weighted imaging, the differences in longitudinal relaxation of different subject are emphasized, but the effect of other characteristics, e.g., the differences in transverse relaxation, may be de-emphasized or depressed. T1 weighted imaging may have short TE and TR times. As another example, T2 weighted imaging exploits the transverse relaxation of the subjects, and de-emphasized or depressed other characteristics, e.g., longitudinal relaxation. T2 weighted imaging may need long TE and TR times. As still another example, proton density weighted imaging may reflect the proton (in the form of water or macromolecules, etc.) concentration of different subjects.

It should be noted that the above description of the spin echo sequence is merely provided for the purposes of illustration, and not intended to limit the scope of the present disclosure. For persons having ordinary skills in the art, multiple variations or modifications may be made under the teachings of the present disclosure. For example, the flip angle of a refocusing RF pulse may be of a value other than 180°; it may be any proper value chosen from 0~180°. As another example, TR or ETL may be changed or selected according to variations or modifications without departing from the scope of the present disclosure.

Figure 6:
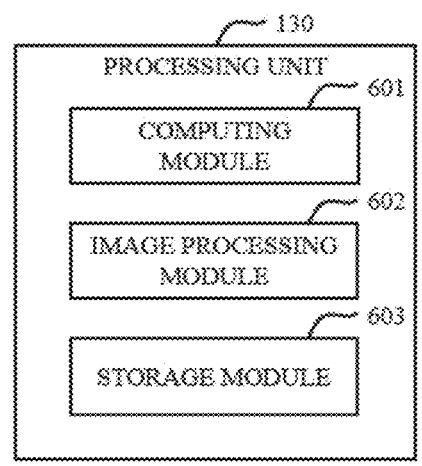
FIG. 6 is a block diagram illustrating a processing unit according to some embodiments of the present disclosure.

FIG. 6 is a block diagram of the processing unit 130 according to some embodiments of the present disclosure. The processing unit 130 as illustrated in FIG. 1 and FIG. 6 may process information before, during, or after an imaging procedure. The processing unit 130 may have some other variations, and FIG. 6 is provided for illustration purposes. The processing unit 130 may be implemented as a central processing unit (CPU), an application-specific integrated circuit (ASIC), an application-specific instruction-set processor (ASIP), a graphics processing unit (GPU), a physics processing unit (PPU), a microcontroller unit, a digital signal processor (DSP), a field programmable gate array (FPGA), an ARM, or the like, or any combination thereof. As shown in FIG. 6, the processing unit 130 may include a computing module 601, an image processing module 602, and a storage module 603.

The computing module 601 may be used for calculating different kinds of information received from the control unit 120 and/or the display unit 140. The information from the control unit 120 may include information about the MRI scanner 110, the gradient magnet field generator 111, the main magnet field generator 113, a subject position (e.g., within an MRI system), the RF transmit/receive unit 112, or the like, or any combination thereof. In some embodiments, the information may be a subject position, the main and/or gradient magnet intensity, the radio frequency phase and/or amplitude, and so on. The information from the display unit 140 may include information from a user and/or other external resource. Exemplary information from a user may include parameters regarding image contrast and/or ratio, an ROI (e.g., the type of tissue to be imaged, etc.), slice thickness, an imaging type (e.g., T1 weighted imaging, T2 weighted imaging, proton density weighted imaging, etc.), T1, T2, a spin echo type (e.g., spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), or the like, or any combination thereof.

The image processing module 602 may process the data such as magnetic resonance (MR) signals acquired from the ROI and reconstruct them into an MR image. The image processing module 602 may or may not include an image reconstruction block. The image processing module 602 may spatially decode MR signals that has been spatially encoded by the magnetic field(s). The intensity or magnitude of the signal, and other properties such as a phase number, a relaxation time (T1 or T2), magnetization transfer, or the like, may be ascertained. The image processing module 602 may employ different kinds of imaging reconstruction techniques for the image reconstruction procedure. The image reconstruction methods may include parallel imaging, Fourier reconstruction, constrained image reconstruction, compressed sensing, or the like, or a variation thereof, or any combination thereof. As for dimensions, the Fourier transformation may include 1-dimensional (1D) Fourier transformation, 2-dimensional (2D) Fourier transformation, 3-dimensional (3D) Fourier transformation. As for types, the Fourier transformation may include discrete Fourier transformation, inverse Fourier transformation, fast Fourier transformation (FFT), non-uniform fast Fourier transformation (NUFFT), partial Fourier transformation, or the like, or any combination thereof. Exemplary algorithms of parallel imaging may include simultaneous acquisition of spatial harmonics (SMASH), sensitivity encoding (SENSE), or the like, or any combination thereof. Exemplary algorithms of partial Fourier transformation may include zero filling, homodyne processing, iterative homodyne processing, or the like, or any combination thereof.

In some embodiments of the present disclosure, the received MR signals, for example, echoes generated by applying a plurality of refocusing RF pulses, may be used for k-space sampling. The k-space sampling may be performed based on encoding gradients applied to the received MR signals. The k-space sampling may include Cartesian sampling, non-Cartesian sampling, or the like. The encoding gradients may include a slice selection gradient, a phase encoding gradient, a frequency encoding gradient, or the like, or any combination thereof. The waveforms of encoding gradients may be periodic, or aperiodic. As to fast imaging, the k-space may be undersampled and one or more undersampled k-space data sets may be generated. The image reconstruction methods described above may be used to reconstruct MR image based on the undersampled data sets. Merely by way of example, an x-direction encoding gradient and a y-direction encoding gradient may be performed on the MR signals simultaneously to generate undersampled k-space data sets. As other examples, the x-direction encoding gradient and the y-direction gradient may be performed sequentially regardless of the order.

The storage module 603 may store the information that may be used by the computing module 601 and/or the image processing module 602. The information may include programs, software, algorithms, data, text, number, images and some other information. These examples are provided here for illustration purposes, and not intended to limit the scope of the present disclosure. Algorithms stored in the storage module 603 may include recursion, a bisection method, an exhaustive search (or brute-force search), a greedy algorithm, a divide and conquer algorithm, a dynamic programming method, an iterative method, a branch-and-bound algorithm, a backtracking algorithm, or the like, or any combination thereof.

It should be noted that the above description of the processing unit is merely provided for the purposes of illustration, and not intended to limit the scope of the present disclosure. For persons having ordinary skills in the art, multiple variations or modifications may be made under the teachings of the present disclosure. For example, the assembly and/or function of processing unit may be varied or changed. In some embodiments, the computing module 601 and the image processing module 602 may share one storage module 603. While in some embodiments, the computing module 601 and the image processing module 602 may have their own storage blocks, respectively. However, those variations and modifications do not depart from the scope of the present disclosure.

Figure 7:
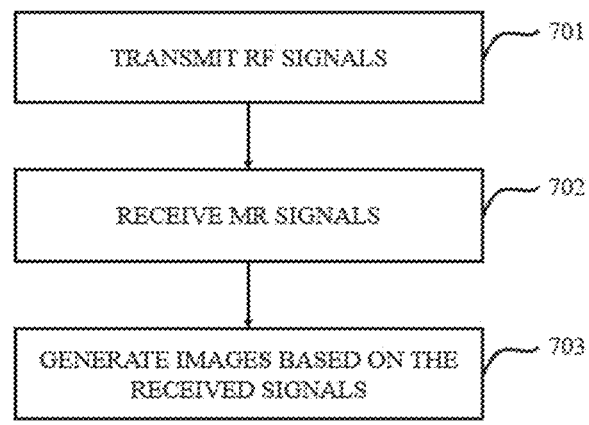
FIG. 7 is a flowchart illustrating a process of a processing unit according to some embodiments of the present disclosure.

FIG. 7 is a flowchart illustrating a process of the processing unit 130 according to some embodiments of the present disclosure. Referring to FIG. 7, RF signals may be transmitted in step 701. The RF signals may be used to excite an ROI of a subject to generate MR signals. In some embodiments, the RF signals may include an excitation RF pulse and a plurality of refocusing RF pulses. Following the RF signals, a plurality of MR signals, for example, a plurality of echoes may be generated. The echoes may either be spin echoes or gradient echoes.

The MR signals generated in step 701 may be received in step 702. In some embodiments, one or more echoes may be received in step 702 by applying encoding gradients on the echoes to spatially encode the echoes. The encoding gradients may include a slice selection gradient, a phase encoding gradient, a frequency encoding gradient, or the like, or any combination thereof. The k-space sampling may be performed based on the processing of the MR signals.

MR images may be generated based on the MR signals received in step 703. In some embodiments, image reconstruction methods may be applied on the MR signals, for example, echoes, to generated MR images. In some embodiments, the echoes described in step 702 may be undersampled so that undersampled k-space data sets may be generated and the k-space may be partially filled. Using an image reconstruction method such as compressed sensing (CS), parallel imaging, and partial Fourier transformation, one or more MR images may be generated.

It should be noted that the flowchart described above is merely provided for the purposes of illustration, and not intended to limit the scope of the present disclosure. For persons having ordinary skills in the art, various modifications and variations may be conducted under the teaching of the present disclosure. However, those modifications and variations may not depart from the scope of the present disclosure.

Figure 8:
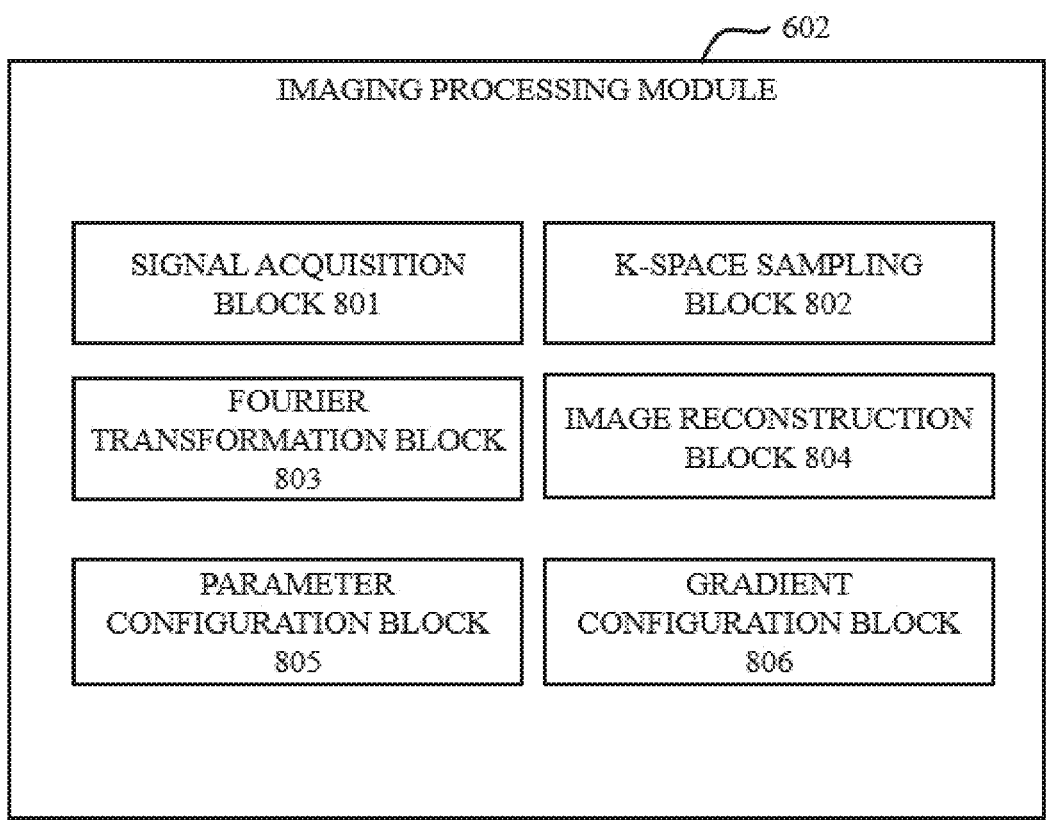
FIG. 8 is a block diagram of an image processing module according to some embodiments of the present disclosure.

FIG. 8 is a block diagram of the image processing module 602 according to some embodiments of the present disclosure. Referring to FIG. 8, the image processing module 602 may include a signal acquisition block 801, a k-space sampling block 802, a Fourier transformation block 803, an image reconstruction block 804, a parameter configuration block 805, and a gradient configuration block 806.

The signal acquisition block 801 may acquire signals, for example, MR signals. The MR signals may include spin echoes, gradient echoes, or the like, or any combination thereof.

The k-space sampling block 802 may perform k-space sampling. In some embodiments of the present disclosure, k-space sampling may be performed based on the MR signals acquired by the signal acquisition block 801.

The Fourier transformation block 803 may preform Fourier transformation. The Fourier transformation may include inverse Fourier transformation, discrete Fourier transformation, fast Fourier transformation, partial Fourier transformation, non-uniform fast Fourier transformation, or the like, or any combination thereof.

The image reconstruction block 804 may generated MR images. In some embodiments of the present disclosure, the MR signals acquired by the signal acquisition block 801 may be undersampled by the k-space sampling block 802 to generate undersampled k-space data sets. The undresampled k-space data sets may be used to generate one or more MR images.

The image reconstruction block 804 may receive the undersampled k-space data sets and perform image reconstruction based on the undersampled k-space data sets. The image reconstruction may be performed based on one or more image reconstruction methods. Exemplary image reconstruction methods may include compressed sensing (CS), parallel imaging, partial Fourier transformation, or the like, or any combination thereof.

The parameter configuration block 805 may set parameters relating to MR images. The parameters may include a reduction factor, an image resolution, image contrast and/or ratio, an ROI, slice thickness, an imaging type (e.g., T1 weighted imaging, T2 weighted imaging, proton density weighted imaging, etc.), T1, T2, a spin echo type (spin echo, fast spin echo (FSE), fast recovery FSE, single shot FSE, gradient recalled echo, fast imaging with stead-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), or the like, or any combination thereof.

The gradient configuration block 806 may control various kinds of gradients applied to MR signals. The gradients may include a slice selection gradient, a phase encoding gradient, a frequency encoding gradient, or the like, or any combination thereof.

It should be noted the description of the image processing module is provided for the purposed of illustration, and not intended to limit the scope of the present disclosure. For persons having ordinary skills in the art, various modifications and variations may be conducted under the teaching of the present disclosure. However, those variations and modifications may not depart from the present disclosure.

Figure 9:
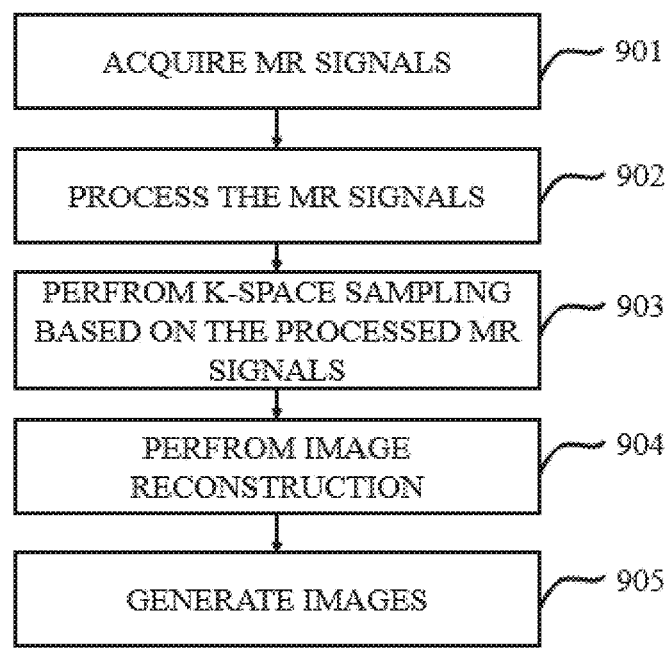
FIG. 9 is a flowchart illustrating an image processing according to some embodiments of the present disclosure.

FIG. 9 is a flowchart illustrating an image processing according to some embodiments of the present disclosure. MR signals may be acquired in step 901. The digitization of MR signals may be called signal acquisition or signal sampling. MR signals received by receiving coils may be radio waves with spatial encoding information, which may belong to analog signals rather than digital signals. In some embodiments, digital signals may propagate more efficiently than analog signals. Digital signals, which may be well-defined and orderly, may be easier for electronic circuits to distinguish from noise, which may be chaotic. This may be one of many advantages of digital signals in communications. Therefore, an analog signal may be converted into a digital signal. Analog to digital conversion may include sampling, holding, quantization, and encoding. In some embodiments, the device for signal acquisition may be an Analog to Digital Converter (ADC). According to the principle of operation, the types of ADC may include direct-conversion ADC, successive approximation ADC, ramp-compare ADC, Wilkinson ADC, integrating ADC, delta-encoded ADC, pipeline ADC, sigma-delta ADC, time-interleaved ADC and time stretch ADC. One or more of the above ADC may be used in the system and method disclosed herein.

It should be noted that the above description is merely provided for the purposes of illustration, and not intended to limit the scope of the present disclosure. For persons having ordinary skills in the art, multiple variations and modifications may be made under the teaching of the present invention. For example, in some embodiments, processes of sampling and holding may combine to make a sampling/holding process. In some embodiments, processes of quantization and encoding may be implemented simultaneously. However, those variations and modifications do not depart from the scope of the present disclosure.

The digitized MR signals may be processed in step 902. In some embodiments, data acquired by analog to digital conversion (ADC data) in step 901 are not used for image reconstruction directly due to lack of some information (e.g. control information, identification information, etc.). Therefore, some information for image reconstruction may need to be added into ADC data. These information may include information about a scan counter, the type of ADC data, the gating data of a physiological signal, or the like, or a combination thereof. The methods to process ADC data may include data registration, pre-processing before reconstruction, or the like, or any combination thereof.

The k-space sampling may be performed based on the processed MR signals in step 903. The k-space sampling may include filling k-space with a plurality of k-space trajectories. The filling method may vary according to certain conditions. For example, the k-space trajectory may be a Cartesian trajectory or a non-Cartesian trajectory. The non-Cartesian trajectory may be radial, spiral, zigzag, propeller, or the like, or any combination thereof. The k-space may be undersampled, oversampled, or fully sampled. The data may be filled into the k-space in any order, such as from the center outward, from left to right, from the top down. The data generated from step 903 may be called k-space data.

It should be noted that the above description is merely provided for the purposes of illustration, and not intended to limit the scope of the present disclosure. For persons having ordinary skills in the art, multiple variations and modifications may be made under the teaching of the present invention. For example, in some embodiments, the k-space may be oversampled in the center region and undersampled in the peripheral region. Alternatively, the k-space may be fully sampled in the center region and undersampled in a peripheral region. It may vary according to certain conditions. However, those variations and modifications do not depart from the scope of the present disclosure.

Inverse Fourier transformation may be performed on the k-space data in step 904. The k-space data may be transformed into frequency-domain data which may be a two-dimensional (2-D) or three-dimensional (3-D) data set. Exemplary image reconstruction methods may include parallel imaging, Fourier reconstruction, constrained image reconstruction, compressed sensing, or the like, or a variation thereof, or any combination thereof. As for dimensions, the Fourier transformation may include 1-dimensional (1D) Fourier transformation, 2-dimensional (2D) Fourier transformation, 3-dimensional (3D) Fourier transformation. As for types, the Fourier transformation may include discrete Fourier transformation, inverse Fourier transformation, fast Fourier transformation (FFT), non-uniform fast Fourier transformation (NUFFT), partial Fourier transformation, or the like, or any combination thereof. Exemplary algorithms of partial Fourier transformation may include zero filling, homodyne processing, iterative homodyne processing, or the like, or any combination thereof. Exemplary algorithms of parallel imaging may include simultaneous acquisition of spatial harmonics (SMASH), AUTO-SMASH, VD-AUTO-SMASH, sensitivity encoding (SENSE), generalized auto-calibrating partially parallel acquisitions (GRAPPA), or the like, or any combination thereof.

In step 905, the frequency-domain data may be processed to generate MR images. In some embodiments, the frequency-domain data may be mapped into optical data for further video processing. For example, in a monochrome display, the frequency-domain data may be mapped into the luminance values of pixels. In a color display, frequency-domain data may be mapped into the luminance and false-color values of pixels. The optical data then may be transformed into signals which drive pixels on a display.

It should be noted that the above description is merely provided for the purposes of illustration, and not intended to limit the scope of the present disclosure. For persons having ordinary skills in the art, multiple variations and modifications may be made under the teaching of the present invention. For example, in some embodiments, after step 905, there may be further processing on generated images, such as geometric transformation and adjustment of image quality. The geometric transformation may include rotation, cropping, mirroring, zooming, or the like, or any combination thereof. The adjustment of image quality may include false-color processing, sharpening, image intensification, or the like, or any combination thereof. However, those variations and modifications do not depart from the scope of the present disclosure.

Figure 10:
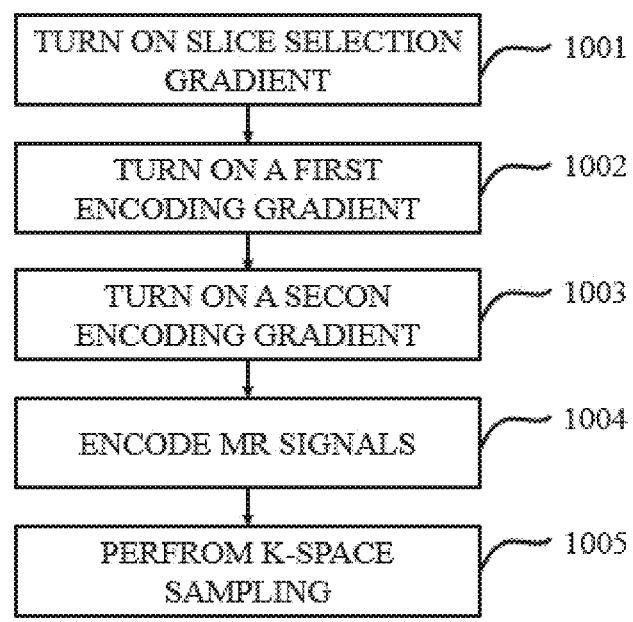
FIG. 10 illustrates a flowchart of k-space sampling according to some embodiments of the present disclosure.

FIG. 10 illustrates a flowchart of the k-space sampling according to some embodiments of the present disclosure. A slice selection gradient may be started in step 1001. The slice selection gradient may select a slice of an ROI. In some embodiments of the present disclosure, the slice selection gradient may be turned on as an RF pulse is applied. The RF pulse may be an excitation RF pulse, a refocusing RF pulse, etc. The slice selection gradient may be turned off when the application of the RF pulse stops.

A first encoding gradient may be turned on in step 1002, and a second encoding gradient may be turned on in step 1003. The first encoding gradient and the second encoding gradient may spatially encode MR signals received by the image processing module as described elsewhere in the present disclosure. In some embodiments, the first encoding gradient may be a phase encoding gradient, and the second encoding gradient may be a frequency encoding gradient. As an example, the phase encoding gradient is applied first and the frequency encoding gradient is applied subsequently. As a result, a Cartesian k-space trajectory may be generated. The Cartesian k-space trajectories may include a certain number of straight lines.

In some embodiments of the present disclosure, the first encoding gradient and the second encoding gradient may be applied simultaneously on MR signals. Accordingly, a non-Cartesian k-space trajectory may be generated. The non-Cartesian k-space trajectory may be radial, spiral, or the like, or a combination thereof. The MR signals may be encoded based on the first encoding gradient and the second encoding gradient in step 1004.

In step 1005, the k-space sampling may be performed based on the encoded MR signals generated in step 1004. Specifically, exemplary trajectories for the k-space sampling may include a Cartesian trajectory or a non-Cartesian trajectory. The non-Cartesian trajectory may be radial, spiral, zigzag, propeller, or the like, or any combination thereof. The k-space may be undersampled, oversampled, or fully sampled. In some embodiments, the k-space may be fully sampled in the center region and undersampled in a peripheral region. As used herein, if the k-space is symmetrical with respect to the line of Ky=0, a center region may refer to the region in which the absolute value of Ky is small. A peripheral region may refer to the region in which the absolute value of Ky is large. The data may be filled into k-space in any order, such as from the center outward, from left to right, from the top down, etc.

It should be noted that the flowchart described above is provided for the purposes of illustration, and not intended to limit the scope of the present disclosure. For persons having ordinary skills in the art, various modifications and variations may be conducted under the teaching of the present disclosure. However, those modifications and variations may not depart from the present disclosure. For example, step 1002 and step 1003 may be performed either concurrently or sequentially.

Figure 11:
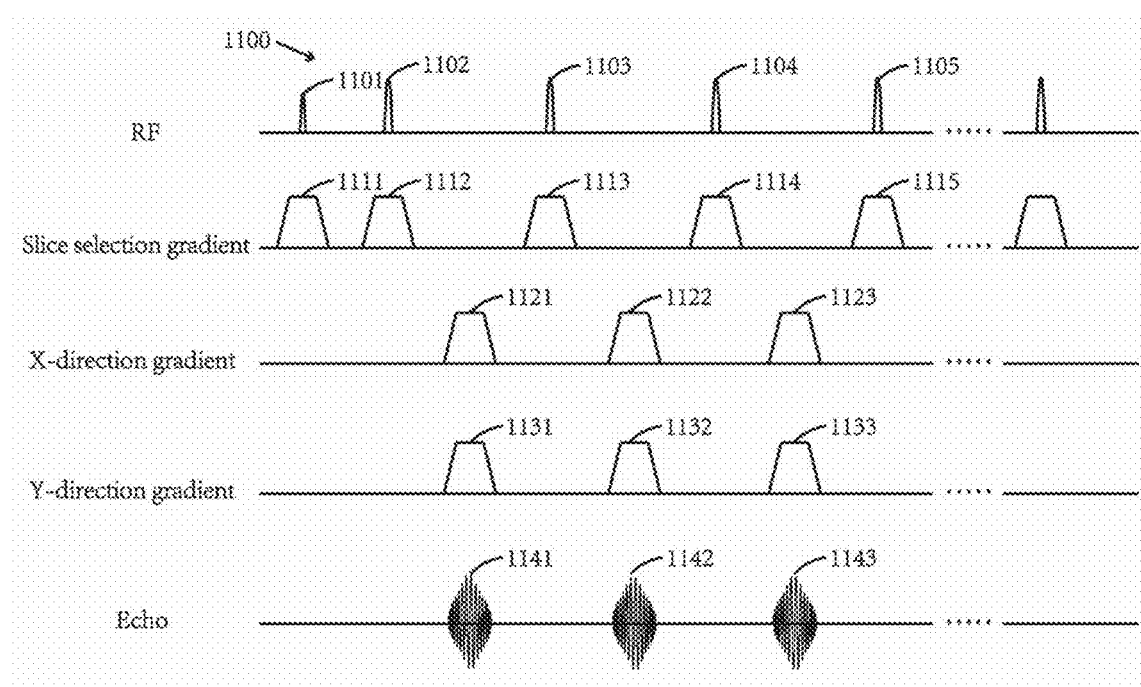
FIG. 11 shows a diagram of a 2D FSE pulse sequence for a single repetition time (TR) according to some embodiments of the present disclosure.

FIG. 11 shows a diagram of a 2D FSE pulse sequence for a single repetition time (TR) according to some embodiments of the present disclosure. The 2D FSE pulse sequence shown in FIG. 11 is suitable for application in the MRI system described elsewhere in the present disclosure. The 2D FSE pulse sequence 1100 may include an excitation RF pulse 1101 and a plurality of refocusing RF pulses, for example, the refocusing RF pulse 1102, the refocusing RF pulse 1103, the refocusing RF pulse 1104, and the refocusing RF pulse 1105. The excitation RF pulse 1101, along with the slice selection gradient 1111 may be used to tip a portion of the longitudinal magnetization of an ROI into the transverse plane. Following the excitation RF pulse 1101, a plurality of refocusing RF pulses may be transmitted to generate a plurality of echoes. A refocusing RF pulse may be accompanied with a slice selection gradient. The number of echoes generated may be determined by the number of refocusing RF pulses.

As illustrated in FIG. 11, the echo 1141 may be generated by the refocusing RF pulse 1112, the echo 1142 may be generated by the refocusing RF pulse 1113, and the echo 1143 may be generated by the refocusing RF pulse 1114. The x-direction encoding gradient and the y-direction encoding gradient may be used to spatially encode the echoes. For example, the x-direction encoding gradient 1121 and the y-direction encoding gradient 1131 may be applied to the echo 1141 so that the echo 1141 is spatially encoded. A spatially encoded echo may correspond to a k-space trajectory. The spatially encoded echo may be used to perform k-space sampling and construct MR images subsequently.

In some embodiments of the present disclosure, an x-direction encoding gradient and a y-direction encoding gradient may be applied to an echo simultaneously to generate a k-space trajectory. It should be noted that the k-space trajectory may include either a straight line or a curve which correspond to Cartesian sampling or non-Cartesian sampling respectively in MRI. The non-Cartesian sampling may include radial sampling and spiral sampling.

It should be noted that the echoes generated by the refocusing RF pulses may be echoes whose flip angles are 180°. In some embodiments of the present disclosure, a flip angle schedule in which flip angles are varied may be applied to the refocusing RF pulses. For example, because of T2-relaxation, the intensity of each echo in one echo train may be different. As used herein, the T2-relaxation may refer to the progressive dephasing of spinning dipoles following the 90° pulse as seen in a spin echo sequence due to tissue-particular characteristics. So if the echo train length (ETL) is 4, in order to decrease the difference among the echoes, the flip angles of the refocusing RF pulses may be set as the values which are less than or equal to 180°, such as 140°, 155°, 165°, 180° in turn.

In 2D FSE, a plurality of echoes may be acquired in a repetition time (TR). In some embodiments, a non-Cartesian coordinate system may be employed in the present disclosure. The slice selection gradient may be applied in the z-direction to select a slice of an ROI to be imaged. The x-direction encoding gradient and the y-direction encoding gradient may be used to spatially encode MR signals, for example echoes, to accomplish the k-space sampling. The k-space sampling may be performed by filling k-space with a certain number of k-space trajectories. Exemplary k-space sampling methods may include Cartesian sampling and non-Cartesian sampling. As for Cartesian sampling, k-space may be filled with Cartesian trajectories, for example, straight lines. As for non-Cartesian sampling, k-space may be filled with non-Cartesian trajectories other than Cartesian trajectories, for example, radial or spiral trajectories. In the process of acquiring an echo, the encoding gradients may be employed in the x and y axes to fill a two-dimension k-space in which Kx and Ky may be used as the coordinates.

During the process of acquiring an echo, the amplitude of the x-direction encoding gradient may be kept either positive or negative. The amplitude of the x-direction encoding gradient when acquiring high spatial frequency information (e.g. edges, details, sharp transitions) of the k-space may be larger than the amplitude of the x-direction encoding gradient when acquiring low spatial frequency information (e.g. contrast, general shapes) of the k-space. From the acquisition of the high spatial frequency information to that of the low spatial frequency information, the amplitude of the x-direction encoding gradient may vary gradually. In some embodiments, the transition from high amplitude to low amplitude of the x-direction encoding gradient may be sharp.

FIGS. 12A-12F show exemplary waveforms of x-direction encoding gradients according to some embodiments of the present disclosure. For further illustrating the present disclosure, several examples are given below, but the examples do not limit the scope of the present disclosure.

Figure 12A:
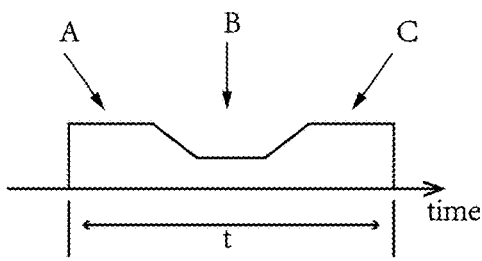
FIGS. 12A-12F show exemplary x-direction encoding gradients according to some embodiments of the present disclosure.

FIG. 12A illustrates an exemplary waveform of an x-direction encoding gradient according to some embodiments of the present disclosure. As illustrated in FIG. 12A, the waveform of the x-direction encoding gradient may include three steady phases (phase A, phase B, and phase C) and two phases of transition. Phase A and phase C may be used to acquire high spatial frequency information in k-space. Phase B may be used to acquire low spatial frequency information in k-space. The letter t may denote the time duration for the acquisition of an echo. The amplitude in phased A, phase B, and phase C may be kept unchanged. The two phases of transition may be linear function. In some embodiments, the two phases of transition may be nonlinear function.

Figure 12B:
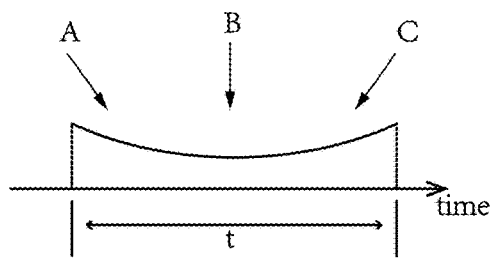

FIG. 12B illustrates an exemplary waveform of an x-direction encoding gradient according to some embodiments of the present disclosure. As illustrated in FIG. 12B, the x-direction encoding gradient may be part of a function that has a smooth variation. The function may be a Gaussian function, a harmonic function, or the like, or any combination thereof. As illustrated in FIG. 12B, the edges of the x-direction encoding gradient (A and C) with larger amplitude may be used to acquire high spatial frequency information. The center region of the x-direction encoding gradient (B) with lower amplitude may be used to acquire low spatial frequency information. The letter t may denote the time duration for the acquisition of an echo.

Figure 12C:
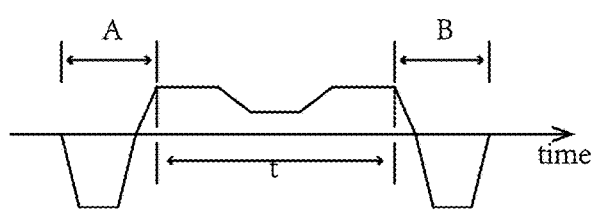
Figure 12D:
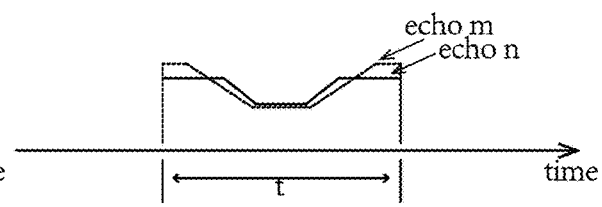
Figure 12E:
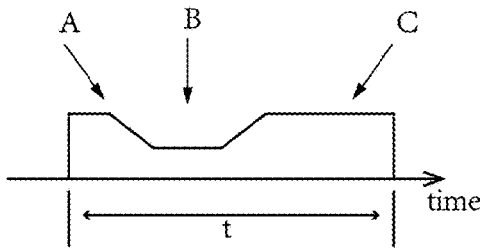
Figure 12F:
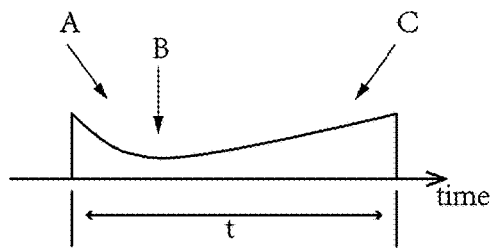

In some embodiments, instead of being symmetric, the waveform of the x-direction encoding gradient may be asymmetric as shown in FIG. 12E and FIG. 12F. The portion as indicated by B in FIG. 12E that has a lower amplitude may be used to acquire low spatial frequency information (e.g., close to the center region of k-space). The portions A and C in FIG. 12E that have higher amplitudes may be used to acquire high spatial frequency information (e.g., a peripheral region of k-space). Likewise, the portion B in FIG. 12F that has lower amplitude may be used to acquire low spatial frequency information (e.g., close to the center region of k-space). The portions A and C in FIG. 12F that have higher amplitude may be used to acquire high spatial frequency information (e.g., a peripheral region of k-space).

In some embodiments, when k-space is undersampled, the x-direction encoding gradient as shown in FIG. 12E and FIG. 12F may be used to perform k-space sampling.

It should be noted that the portion that has lower amplitude of an x-direction encoding gradient may be located in anywhere in the waveform of the x-direction encoding gradient, for example, in the center of the waveform, in the left of the waveform, or in the right of the waveform.

It should be noted that the above description of the waveforms of the x-direction encoding gradient are merely provided for the purposes of illustration, and not intended to limit the scope of the present disclosure. For persons having ordinary skills in the art, multiple variations and modifications may be made under the teachings of the present disclosure. For example, in some embodiments, the time duration for acquiring high spatial frequency information and low spatial frequency information of k-space for an x-direction encoding gradient may be equal or unequal. As other examples, the time of acquiring high spatial frequency information may be longer or shorter than that of acquiring low spatial frequency information. However, those variations and modifications do not depart from the scope of the present disclosure.

In some embodiments, there may be a dephasing gradient before the application of an x-direction encoding gradient and/or the application of a rephrasing gradient after an x-direction encoding gradient. In the process of acquiring an echo, the dephasing gradient may be used to determine the starting point of a k-space trajectory of the echo. The rephasing gradient may adjust the state of the echo. In some embodiments, the rephasing gradient may eliminate the effects caused by the dephasing gradient.

For further understanding the present disclosure, several examples are given below, but the examples do not limit the scope of the present disclosure. FIG. 12C illustrates exemplary waveforms of an x-direction dephasing gradient, an x-direction rephrasing gradient, and an x-direction encoding gradient according to some embodiments of the present disclosure. As shown in FIG. 12C, the waveform of the first encoding gradient that includes three steady phases and two phases of transition may be used to acquire an echo. The letter A may denote a dephasing gradient, and the letter B may denote a rephasing gradient. The letter t may denote the time duration for the acquisition of an echo. The amplitudes of the dephasing gradient and the rephasing gradient may have a same direction (positive or negative). Alternatively, the amplitudes of the dephasing gradient and the rephasing gradient may have opposite directions (positive or negative). Exemplary waveforms of the dephasing gradient and the rephasing gradient may be a trapezoidal wave, a square wave, a triangular wave, or the like, or a combination thereof.

It should be noted that the above description of the dephasing gradient and the rephasing gradient is merely provided for the purposes of illustration, and not intended to limit the scope of the present disclosure. For persons having ordinary skills in the art, multiple variations and modifications may be made under the teachings of the present disclosure. For example, the dephasing gradients in x-direction of two successive echoes may be slightly different in amplitude. For example, in some embodiments, when different echoes are acquired, the dephasing gradients may be adjusted to make the starting points of the k-space trajectories different. However, those variations and modifications do not depart from the scope of the present disclosure.

The x-direction encoding gradients, which are employed to acquire different echoes, may have the same pattern or different patterns. In some embodiments, the patterns of the x-direction encoding gradients may be made different by adjusting the amplitudes, the waveforms, the time duration for the acquisition of an echo and/or the time duration of each phrase.

For further understanding the present disclosure, several examples are given below, but the examples do not limit the scope of the present disclosure. FIG. 12D illustrates waveforms of two successive x-direction encoding gradients that may be used to acquire two successive echoes according to some embodiments of the present disclosure. As illustrated in FIG. 12D, the solid line may denote the x-direction encoding gradient that may be used to acquire echo n, and the dash line may denote the x-direction encoding gradient that may be used to acquire echo m. The letter t may denote the time duration for the acquisition of an echo. Both the two x-direction encoding gradients have three steady phases and two phases of transition. However, they may have different amplitudes and different time intervals for each phase. As shown in FIG. 12D, the amplitude of the first steady phase of the x-direction encoding gradient for echo m may be larger than that of echo n. The time interval for the phase of transition of the x-direction encoding gradient for echo m may be longer than that of echo n. The time for acquiring the high spatial frequency information of the x-direction encoding gradient for echo m may be shorter than that of echo n. The time for acquiring the low spatial frequency information of the x-direction encoding gradient for echo m may be longer than that of echo n.

It should be noted that the above description of the waveforms of the x-direction encoding gradients is merely provided for the purposes of illustration, and not intended to limit the scope of the present disclosure. For persons having ordinary skills in the art, multiple variations and modifications may be made under the teachings of the present disclosure. For example, the waveforms of the x-direction encoding gradients for acquiring different echoes may be different. In some embodiments, the x-direction encoding gradient for echo m may include three steady phases and two phases of transition. While the x-direction encoding gradient for echo n may be part of a smooth function. However, those variations and modifications do not depart from the scope of the present disclosure.

In some embodiments of the present disclosure, when acquiring an echo, a y-direction encoding gradient may be applied simultaneously with an x-direction encoding gradient. In the process of echo acquisition, the amplitude of the y-direction encoding gradient may oscillate around zero, and the k-space trajectory may oscillate around a baseline as well. The baseline may correspond to a value of Ky in the k-space. The oscillation of the amplitude of the y-direction encoding gradient may be periodic or aperiodic.

Figure 13A:
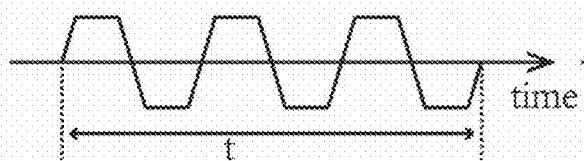
FIGS. 13A-13F show exemplary y-direction encoding gradients according to some embodiments of the present disclosure.
Figure 13B:
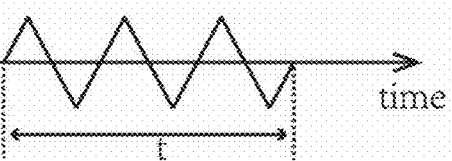

For further illustrating the present disclosure, several examples are given below, but the examples do not limit the scope of the present disclosure. FIG. 13A illustrates an exemplary waveform of a y-direction encoding gradient according to some embodiments of the present disclosure. As illustrated in FIG. 13A, the y-direction encoding gradient may be a trapezoidal wave. The amplitude of the y-direction encoding gradient oscillates periodically. The letter t may denote the time duration for the acquisition of an echo. FIG. 13B illustrates an exemplary waveform of a y-direction encoding gradient according to some embodiments of the present disclosure. As illustrated in in FIG. 13B, the y-direction encoding gradient may be a triangular wave. The amplitude of the y-direction encoding gradient oscillates periodically. The letter t may be the duration of the acquisition of one echo.

It should be noted that the above description of the waveforms of the y-direction encoding gradients are merely provided for the purposes of illustration, and not intended to limit the scope of the present disclosure. For persons having ordinary skills in the art, multiple variations and modifications may be made under the teachings of the present disclosure. For example, in some embodiments, the waveform of the y-direction encoding gradient may be a sawtooth wave, a square wave, a sinusoidal wave, or the like, or any combination thereof. In some embodiments, within one period, the waveform of the y-direction encoding gradient may be a mixture of any waves mentioned above. In some embodiments, within one period, there may be one kind of waveform but with different amplitudes. In some embodiments, the amount of the period in the duration of the acquisition of one echo may be one, two, three, or more. However, those variations and modifications do not depart from the scope of the present disclosure.

Figure 13C:
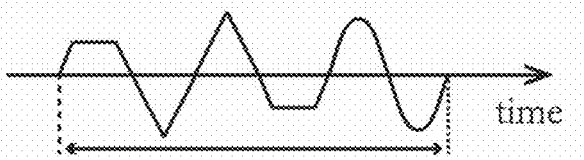

FIG. 13C illustrates an exemplary waveform of a y-direction encoding gradient according to some embodiments of the present disclosure. As shown in FIG. 13C, the y-direction encoding gradient is a mixture of a trapezoidal wave, a triangular wave, and a sinusoidal wave in the time duration for the acquisition of an echo. The y-direction encoding gradient may oscillate in an aperiodic way. The letter t may denote the time duration for the acquisition of an echo.

It should be noted that the above description of the y-direction encoding gradient is merely provided for the purposes of illustration, and not intended to limit the scope of the present disclosure. For persons having ordinary skills in the art, multiple variations and modifications may be made under the teachings of the present disclosure. For example, the y-direction encoding gradient may oscillate in a random way as what is described in FIG. 13C. In addition, the y-direction encoding gradient may oscillate in an aperiodic but regular way. For instance, in some embodiments, the y-direction encoding gradient may oscillate in a way where the amplitude of the y-direction encoding gradient may vary (increase or decrease) gradually. However, those variations and modifications do not depart from the scope of the present disclosure.

The y-direction encoding gradients for acquiring different echoes, for example, two successive echoes, may be the same or different. In some embodiments, when different echoes are acquired, the patterns of the y-direction encoding gradients may be made different by adjusting the amplitudes, the waveforms, the time duration for the acquisition of an echo and/or the oscillating method of the y-direction encoding gradients.

Figure 13D:
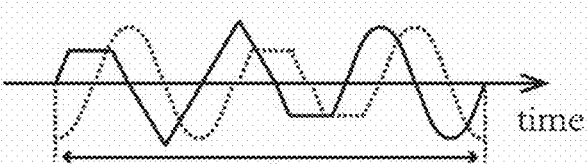

For further understanding the present disclosure, several examples are given below, but the examples do not limit the scope of the present disclosure. FIG. 13D illustrates waveforms of two exemplary y-direction encoding gradients for acquiring different echoes according to some embodiments of the present disclosure. As shown in FIG. 13D, the solid line may denote the waveform of the y-direction encoding gradient for a first echo. The dash line may denote the waveform of the y-direction encoding gradient for a second echo other than the first echo. The letter t may denote the time duration for the acquisition of an echo. The y-direction encoding gradient for acquiring the first echo may be a mixture of, for example, a trapezoidal wave, a sawtooth wave, and a sinusoidal wave within the time duration for the acquisition of an echo. The y-direction encoding gradient for the first echo may oscillate in an aperiodic way. The y-direction encoding gradient for the second echo may be a mixed wave as well, which may include the combination of a trapezoidal wave, a sawtooth wave, and a sinusoidal wave within the time duration for the acquisition of an echo. However, the two y-direction encoding gradients may be different in terms of amplitude and/or a time interval of a phase. The y-direction encoding gradient for the second echo may oscillate in an aperiodic way.

It should be noted that the above description of the waveforms of the y-direction encoding gradients are merely provided for the purposes of illustration, and not intended to limit the scope of the present disclosure. For persons having ordinary skills in the art, multiple variations and modifications may be made under the teachings of the present disclosure. For example, the y-direction encoding gradients used to acquire different echoes may be different in the amplitude, the waveforms, the amount of the periods in the time duration for the acquisition of an echo, the oscillating method (periodic or aperiodic), or the like, or any combination thereof. However, those variations and modifications do not depart from the scope of the present disclosure.

In some embodiments, there may be a dephasing gradient before the application of a y-direction encoding gradient. In the process of acquiring an echo, the value of Ky of the baseline may be determined by the dephasing gradient. For different echoes, the values of Ky of the baselines may be the same or different.

Figure 13E:
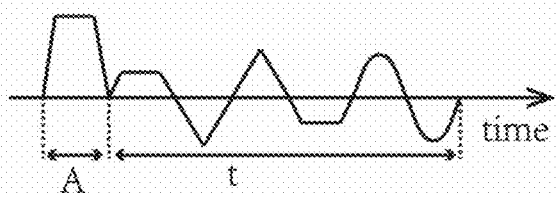

For further illustrating the present disclosure, several examples are given below, but the examples do not limit the scope of the present disclosure. FIG. 13E illustrates an exemplary y-direction encoding gradient according to some embodiments of the present disclosure. As shown in FIG. 13E, an aperiodic waveform including a combination of a triangular wave, a trapezoidal wave, and a sinusoidal wave may be used to acquire an echo. The letter A may denote the dephasing gradient. The letter t may denote the time duration for the acquisition of an echo.

In some embodiments, there may be a rephasing gradient after the application of a y-direction encoding gradient. The rephasing gradient may adjust the state of the signal. In some embodiments, the rephasing gradient may eliminate the effects caused by a dephasing gradient.

Figure 13F:
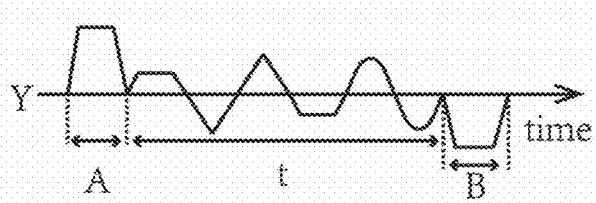

For further illustrating the present disclosure, several examples are given below, but the examples do not limit the scope of the present disclosure. FIG. 13F illustrates an exemplary y-direction encoding gradient according to some embodiments of the present disclosure. As shown in FIG. 13F, the y-direction encoding gradient may be an aperiodic waveform including a triangular wave, a trapezoidal wave, and a sinusoidal wave. The letter A may denote the dephasing gradient, and the letter B may denote the rephasing gradient. The letter t may denote the time duration for the acquisition of an echo.

It should be noted that the above description about distribution of the density of the baseline is merely provided for the purposes of illustration, and not intended to limit the scope of the present disclosure. For persons having ordinary skills in the art, multiple variations and modifications may be made under the teachings of the present disclosure. For example, in some embodiments, the amplitudes of the dephasing gradient and the rephasing gradient may be same in direction (positive or negative). Alternatively, the amplitudes of the dephasing gradient and the rephasing gradient may be opposite in direction. The waveforms of the dephasing gradient and the rephasing gradient may be trapezoidal wave, square wave, triangular wave, or the like. However, those variations and modifications do not depart from the scope of the present disclosure.

The distribution of the density of the baselines in the k-space may be set by employing different dephasing gradients when different echoes are acquired.

Figure 14:
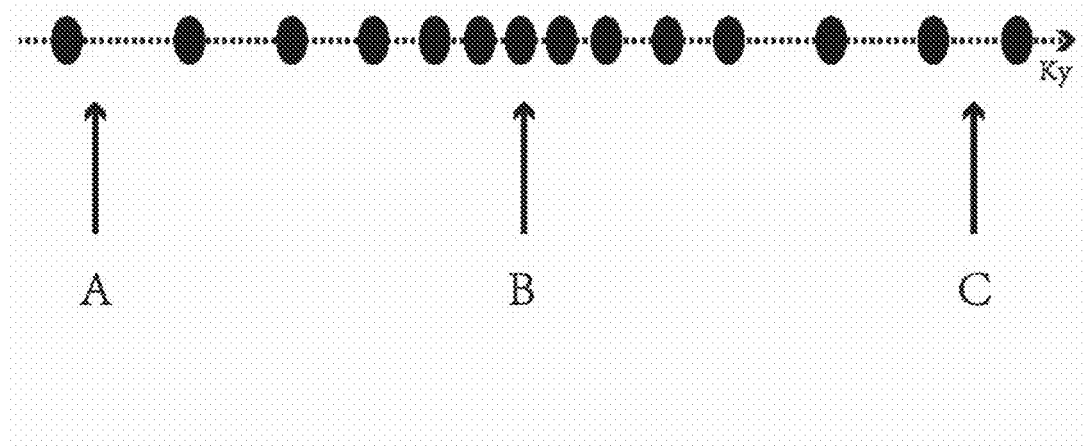
FIG. 14 is an exemplary diagram illustrating the distribution of baselines of the k-space trajectory according to some embodiments of the present disclosure.

FIG. 14 illustrates an exemplary diagram of the distribution of baselines of the k-space trajectory according to some embodiments of the present disclosure. As shown in FIG. 14, the dots horizontally arranged may denote the values of Ky corresponding to baselines. The letter A and the letter C may denote the peripheral regions of the k-space corresponding to the high frequency area, and the letter B may denote the center regions of k-space corresponding to low frequency area. In FIG. 14, in the low frequency area of the k-space, the density of the baselines may be higher than that in the high frequency area.

It should be noted that the above description about distribution of the density of the baseline is merely provided for the purposes of illustration, and not intended to limit the scope of the present disclosure. For persons having ordinary skills in the art, multiple variations and modifications may be made under the teachings of the present disclosure. For example, in some embodiments, the density of the baseline may be uniform. In some embodiments, the density of the baseline may vary in another ways. For instance, the density of the baselines may vary (increase or decrease) gradually form one side to the other side. In some embodiments, the density of the baselines may be low in the center region of the k-space and high in the peripheral region of the k-space. In some embodiments, the density of the baselines may distribute in an alternating way. In some embodiments, the density of the baseline may also distribute in a random way. However, those variations and modifications do not depart from the scope of the present disclosure.

Figure 15:
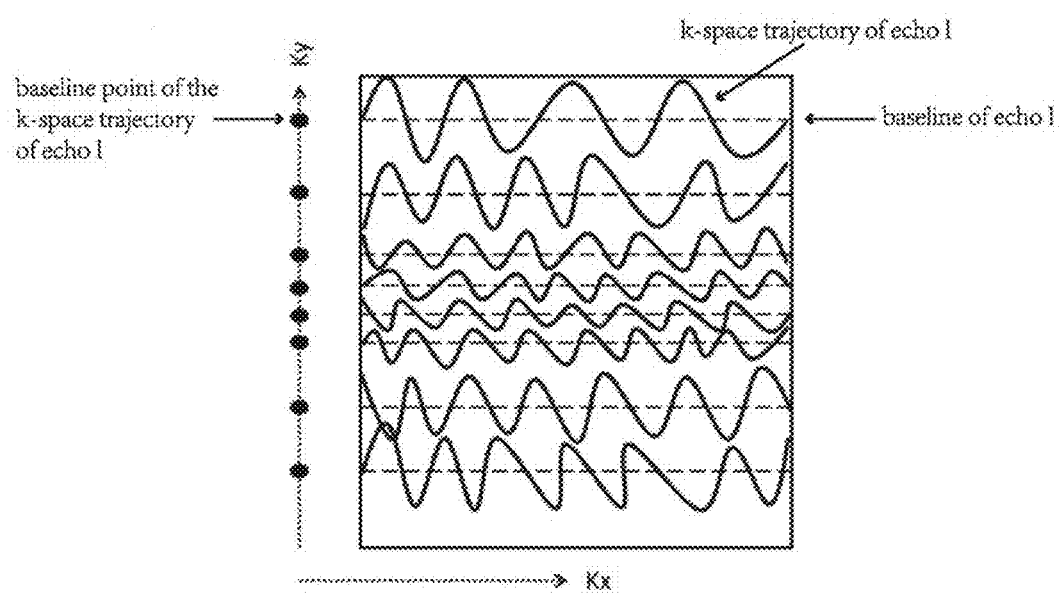
FIG. 15 is an exemplary diagram of k-space sampling according to some embodiments of the present disclosure.

FIG. 15 is an exemplary diagram of the k-space sampling according to some embodiments of the disclosure. The k-space may be sampled by eight k-space trajectories which are non-Cartesian sampling. It should be noted that the amount of echoes used to perform the k-space sampling and the distribution of baselines in the k-space may be preset. The distribution of baselines may be adjusted based on the value of Ky that may be controlled by a dephasing gradient that is described elsewhere in the present disclosure.

In FIG. 15, the vertically distributed black spots may indicate values of Ky corresponding to baselines as indicated by dotted straight lines vertically arranged in k-space. A solid line may indicate a k-space trajectory of an echo. A k-space trajectory may oscillate based on its baseline. In the peripheral region of k-space corresponding to the high frequency area of k-space, the density of baselines may be lower than that in the center region of k-space corresponding to the low frequency area. The amplitude of the k-space trajectories may correlate to the density of the baselines in k-space. As shown in FIG. 15, in the area where the density of the baselines is low, k-space trajectories may fluctuate sharply. In the area where the density of the baselines is high, k-space trajectories may fluctuate gradually. As shown in FIG. 15, the waveforms of the k-space trajectories may be different, but they all oscillate based on the baselines.

EXAMPLES

For further understanding the present disclosure, several examples are given below, but the examples do not limit the scope of the present disclosure.

Figure 16:
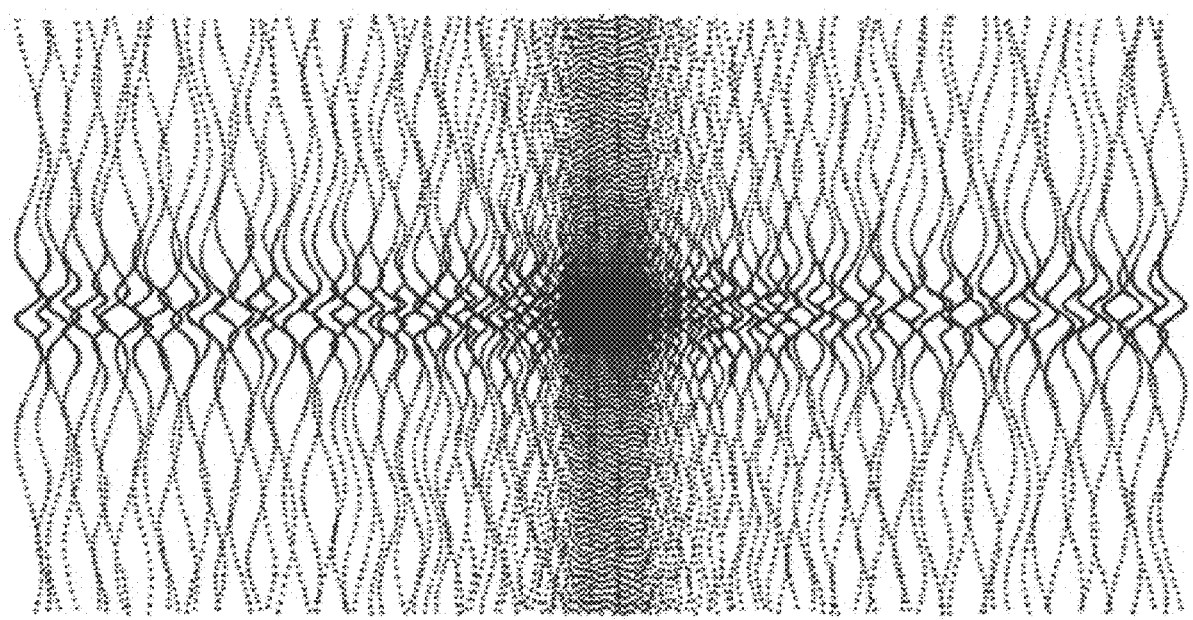
FIG. 16 illustrates an exemplary diagram of k-space sampling for water phantom according to some embodiments of the present disclosure.

FIG. 16 illustrates an exemplary diagram of k-space sampling for water phantom according to some embodiments of the present disclosure. As illustrated in FIG. 16, a 2D FSE sequence was used to obtain an MR image. The size of k-space was 408×408. The reduction factors in the Kx-direction and the Ky-direction were both 3.2. The total reduction factor was 10. One hundred twenty-eight echoes were generated and used for the k-space sampling. The ADC acquired 128 data points from an echo.

It should be noted that the above description is merely provided for the purposes of illustration, and not intended to limit the scope of the present disclosure. For persons having ordinary skills in the art, multiple variations and modifications may be made under the teachings of the present disclosure. For example, the original size of k-space, the reduction factor, the amount of the acquired echoes and the amount of data points acquired from an echo may be changed or selected according to variations or modifications without departing from the scope of the present disclosure.

Figure 17A:
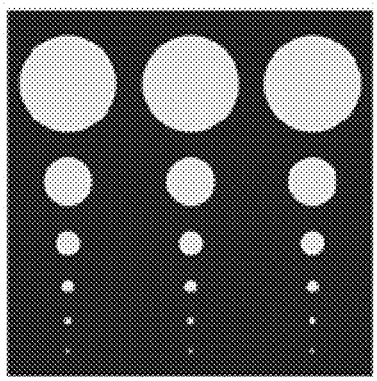
FIGS. 17A-17C illustrate MR images for resolution water phantom according to some embodiments of the present disclosure.
Figure 17B:
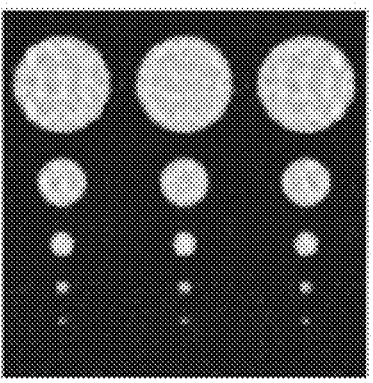
Figure 17C:
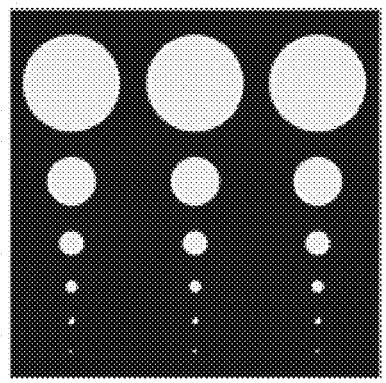

FIG. 17A illustrates the original image of the resolution water phantom. FIG. 17B illustrates the image of the resolution water phantom reconstructed by non-uniform fast Fourier transformation (NUFFT). FIG. 17C illustrates the image of the resolution water phantom reconstructed by compressed sensing.

As shown in FIG. 17B, compared to the original image of the Shepp Logan water phantom, when the k-space data obtained according to the undersampling pattern in FIG. 16 were reconstructed by nonuniform fast Fourier transformation (NUFFT) and zero filling, the reconstructed image is unclear, and some spots in the original image may hardly be seen in the reconstructed image.

As shown in FIG. 17C, when the k-space data obtained according to the undersampling pattern in FIG. 16 were reconstructed by compress sensing, the details of the original image may be restored in the reconstructed image.

Figure 18A:
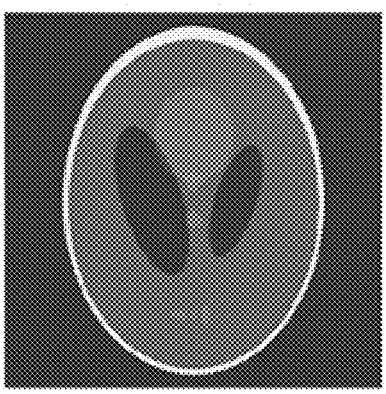
FIGS. 18A-18C illustrate MR images for Shepp Logan water phantom according to some embodiments of the present disclosure.
Figure 18B:
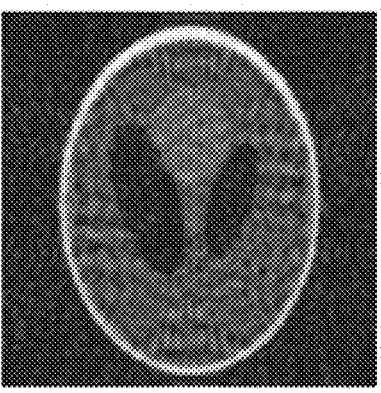
Figure 18C:
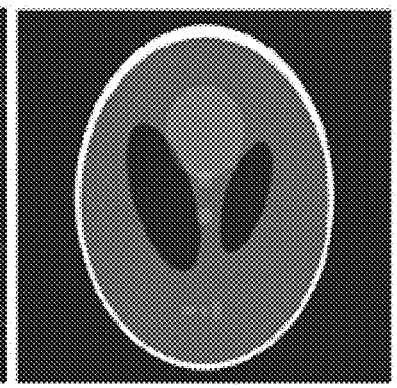

FIG. 18A illustrates the original image of the Shepp Logan water phantom. FIG. 18B illustrates the image of the Shepp Logan water phantom reconstructed by nonuniform fast Fourier transformation (NUFFT) and zero filling. FIG. 18C illustrates the image of the Shepp Logan water phantom reconstructed based on compressed sensing.

As shown in FIG. 18B, compared to the original image of the Shepp Logan water phantom, if the k-space data obtained according to the undersampling pattern in FIG. 16 were reconstructed by nonuniform fast Fourier transformation (NUFFT) and using zero to replace the data which was not sampled, the reconstructed image is unclear, and some spots in the original image may hardly be seen in the reconstructed image.

As shown in FIG. 18C, when the k-space data obtained according to the undersampling pattern in FIG. 16 were reconstructed by compress sensing, the details of the original image may be restored in the reconstructed image.

Figure 19:
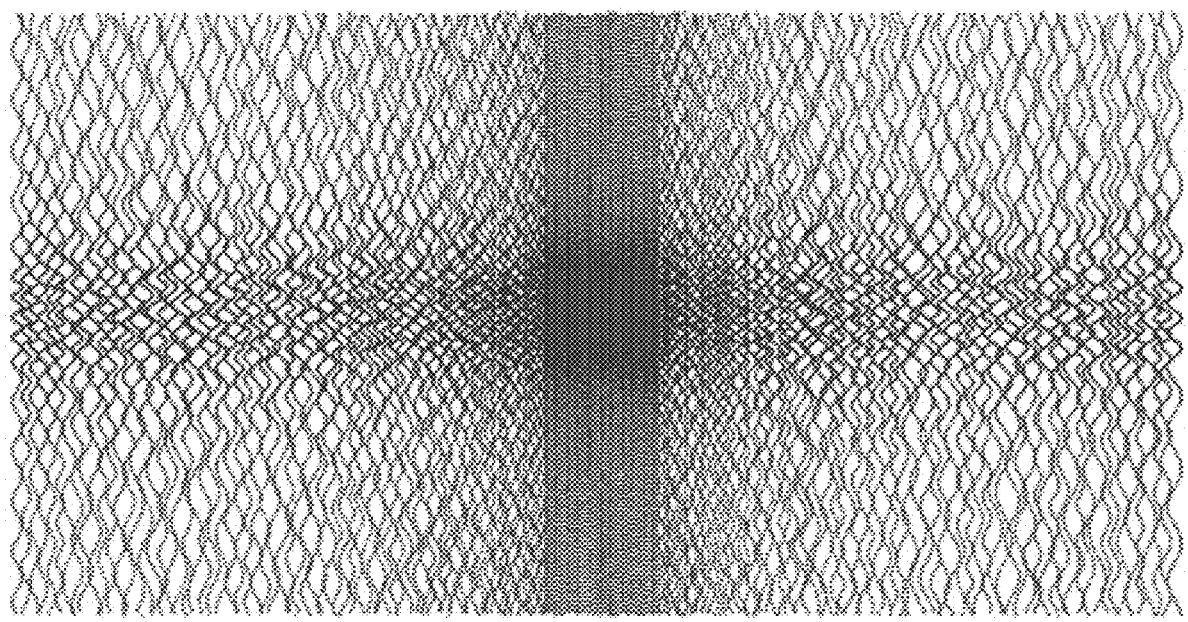
FIG. 19 illustrates an exemplary diagram of k-space sampling for a knee according to some embodiments of the present disclosure.

FIG. 19 illustrates an exemplary diagram of the k-space sampling for a knee according to some embodiments of the present disclosure. Referring to FIG. 19, a 2D FSE sequence was used to obtain MR images. The original size of k-space was 384×384. The reduction factors in Kx and Ky-direction were both 2. The total reduction factor was 4. One hundred ninety-two echoes were generated and used for k-space sampling. The ADC acquired 192 data points from an echo.

It should be noted that the above description is merely provided for the purposes of illustration, and not intended to limit the scope of the present disclosure. For persons having ordinary skills in the art, multiple variations and modifications may be made under the teachings of the present disclosure. For example, the original size of k-space, the reduction factor, the amount of the acquired echoes and the amount of data points acquired from an echo may be changed or selected according to variations or modifications without departing from the scope of the present disclosure.

Figure 20A:
FIGS. 20A-20C illustrate MR images for knees according to some embodiments of the present disclosure.
Figure 20B:
Figure 20C:

FIG. 20A illustrates the original image of the knee. FIG. 20B illustrates the image of the knee reconstructed by nonuniform fast Fourier transformation (NUFFT). FIG. 20C illustrates the image of the knee reconstructed by compressed sensing.

As shown in FIG. 20B, compared to the original image of the knee, if the k-space data obtained according to the undersampling pattern in FIG. 19 were reconstructed by nonuniform fast Fourier transformation (NUFFT) and zero filling, the reconstructed image is unclear.

As shown in FIG. 20C, when the k-space data obtained according to the undersampling pattern in FIG. 19 were reconstructed by compress sensing, the details of the original image may be restored in the reconstructed image.

It should be noted that the above description is merely provided for the purposes of illustration, and not intended to limit the scope of the present disclosure. For persons having ordinary skills in the art, multiple variations and modifications may be made under the teachings of the present disclosure. For example, the non-Cartesian sampling disclosed in this disclosure may combine with techniques including parallel imaging, compressed sensing, partial Fourier transformation, or the like, or any combination thereof. However, those variations and modifications do not depart from the scope of the present disclosure.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

What is claimed is:

1. A method for generating a magnetic resonance (MR) image, the method comprising:

generating a main magnetic field through a region of interest (ROI);
   applying a slice selection gradient to a slice of the ROI;
   applying a plurality of radio frequency (RF) pulses to the slice of the ROI to generate a plurality of echoes;
   applying a first encoding gradient in a first direction and simultaneously applying a second encoding gradient in a second direction on each of the plurality of echoes;
   generating, based on the first encoding gradient in the first direction and the second encoding gradient in the second direction, a plurality of undersampled k-space data sets, wherein the plurality of undersampled k-space data sets correspond to a plurality of k-space trajectories each of which corresponds to one of the plurality of echoes and oscillates based on a baseline, a distribution density of the baselines associated with a center region of the k-space being larger than a distribution density of the baselines associated with a peripheral region of the k-space, the baselines corresponding to the plurality of k-space trajectories being parallel to each other; and
   generating an MR image by applying at least one image reconstruction method to the plurality of undersampled k-space data sets.

2. A magnetic resonance imaging (MRI) system comprising: an MRI scanner and a processing unit, the MRI scanner comprising:

a main magnet field generator configured to generate a main magnetic field through a region of interest (ROI);
   a gradient magnet field generator configured to apply a slice selection gradient to a slice of the ROI, to generate a first encoding gradient in a first direction, and to generate a second encoding gradient in a second direction; and
   a radio frequency (RF) transmit/receive unit configured to transmit a plurality of RF pulses to the slice of the ROI to generate a plurality of echoes, said gradient magnet field generator being configured to apply the first encoding gradient in the first direction and the second encoding gradient in the second direction simultaneously on each of the plurality of echoes;
   wherein the processing unit is configured to generate a plurality of undersampled k-space data sets based on the first encoding gradient in the first direction and the second encoding gradient in the second direction, and generate a magnetic resonance (MR) image by applying at least one image reconstruction method to the plurality of undersampled k-space data sets, the plurality of undersampled k-space data sets corresponding to a plurality of k-space trajectories each of which corresponds to one of the plurality of echoes and oscillates based on a baseline, a distribution density of the baselines associated with a center region of the k-space being larger than a distribution density of the baselines associated with a peripheral region of the k-space, the baselines corresponding to the plurality of k-space trajectories being parallel to each other.

3. The method of claim 1, a waveform of the first encoding gradient in the first direction comprising three steady phases and two phases of transition.

4. The method of claim 1, a waveform of the first encoding gradient in the first direction comprising part of a function having a smooth variation.

5. The method of claim 1, the second encoding gradient in the second direction comprising an oscillating waveform.

6. The method of claim 1, the applying the first encoding gradient in the first direction comprising:

applying at least two different encoding gradients for two different echoes, respectively.

7. The method of claim 1, the first encoding gradient in the first direction further comprising at least one of a dephasing gradient and a rephasing gradient.

8. The method of claim 1, the second encoding gradient in the second direction further comprising at least one of a dephasing gradient and a rephasing gradient.

9. The method of claim 1, wherein
an amplitude of the first encoding gradient is always positive or always negative during a process of acquiring each of the plurality of echoes, and
an absolute value of the amplitude of the first encoding gradient for acquiring the center region of the k-space is lower than an absolute value of the amplitude of the first encoding gradient for acquiring the peripheral region of the k-space.

10. The MRI system of claim 2, the plurality of RF pulses comprising fast spin echo (FSE).

11. The MRI system of claim 2, a waveform of the first encoding gradient in the first direction comprising three steady phases and two phases of transition.

12. The MRI system of claim 11, an amplitude of the waveform of the first encoding gradient in the first direction comprising three steady phases and two phases of transition.

13. The MRI system of claim 2, a waveform of the first encoding gradient in the first direction comprising part of a function having a smooth variation.

14. The MRI system of claim 13, an amplitude of the waveform of the first encoding gradient in the first direction comprising part of a function having a smooth variation.

15. The MRI system of claim 2, the second encoding gradient in the second direction comprising an oscillating waveform.

16. The MRI system of claim 2, the applying the first encoding gradient in the first direction comprising:
applying at least two different encoding gradients for two different echoes, respectively.

17. The MRI system of claim 2, the first encoding gradient in the first direction further comprising at least one of a dephasing gradient or a rephasing gradient.

18. The MRI system of claim 2, the second encoding gradient in the second direction further comprising at least one of a dephasing gradient or a rephasing gradient.

19. The MRI system of claim 2, wherein
an amplitude of the first encoding gradient is always positive or always negative during a process of acquiring each of the plurality of echoes, and
an absolute value of the amplitude of the first encoding gradient for acquiring the center region of the k-space is lower than an absolute value of the amplitude of the first encoding gradient for acquiring the peripheral region of the k-space.

20. The method of claim 1, wherein at least one of the plurality of k-space trajectories is continuous and traverses the k-space along at least one axis of the k-space.

* * * * *